United States Patent
Handler

(10) Patent No.: US 11,738,145 B2
(45) Date of Patent: Aug. 29, 2023

(54) MEDICAL DEVICE DATA INTEGRATION APPARATUS AND METHODS

(71) Applicants: BAXTER INTERNATIONAL INC., Deerfield, IL (US); BAXTER HEALTHCARE SA, Glattpark (CH)

(72) Inventor: Jonathan Alan Handler, Northbrook, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 0 days.

(21) Appl. No.: 18/070,098

(22) Filed: Nov. 28, 2022

(65) Prior Publication Data

US 2023/0089041 A1 Mar. 23, 2023

Related U.S. Application Data

(60) Continuation of application No. 17/027,098, filed on Sep. 21, 2020, now Pat. No. 11,511,041, which is a
(Continued)

(51) Int. Cl.
*G08C 19/22* (2006.01)
*A61M 5/172* (2006.01)
(Continued)

(52) U.S. Cl.
CPC .......... *A61M 5/1723* (2013.01); *G16H 20/40* (2018.01); *G16H 40/67* (2018.01); *H04L 67/12* (2013.01);
(Continued)

(58) Field of Classification Search
CPC ........ A61M 5/1723; A61M 2205/3303; A61M 2205/3561; A61M 2205/502;
(Continued)

(56) References Cited

U.S. PATENT DOCUMENTS 7,039,878 B2   5/2006 Auer et al.
8,182,440 B2   5/2012 Cruz et al.
(Continued)

FOREIGN PATENT DOCUMENTS

CN   1518718      8/2004
WO   2014210465   12/2014

OTHER PUBLICATIONS

EP OA Application No. 16 837 596.2-1126 dated Dec. 7, 2022—2 pages.
(Continued)

*Primary Examiner* — Toan N Pham
(74) *Attorney, Agent, or Firm* — K&L Gates LLP

(57) ABSTRACT

Methods, systems, and apparatuses for integrating medical device data are disclosed. In an example embodiment, a processor receives infusion therapy progress data that is generated by an infusion pump and renal failure therapy progress data that is generated by a renal failure therapy machine. The processor also receives physiological data that generated by at least one physiological sensor. The processor determines fluid balance data based on a difference between the infusion therapy progress data and the renal failure therapy progress data. The processor displays the fluid balance data in conjunction with hemodynamic information from the physiological data.

20 Claims, 14 Drawing Sheets

Related U.S. Application Data continuation of application No. 16/679,803, filed on Nov. 11, 2019, now Pat. No. 10,780,224, which is a continuation of application No. 16/126,366, filed on Sep. 10, 2018, now Pat. No. 10,471,208, which is a division of application No. 15/235,701, filed on Aug. 12, 2016, now Pat. No. 10,071,202.

(60) Provisional application No. 62/205,104, filed on Aug. 14, 2015.

(51) Int. Cl.
    *H04L 67/12* (2022.01)
    *G16H 40/67* (2018.01)
    *G16H 20/40* (2018.01)
    *H04L 67/56* (2022.01)

(52) U.S. Cl.
    CPC ..... *H04L 67/56* (2022.05); *A61M 2205/3303* (2013.01); *A61M 2205/3561* (2013.01); *A61M 2205/502* (2013.01); *A61M 2205/6009* (2013.01); *A61M 2210/1082* (2013.01)

(58) Field of Classification Search
    CPC .. A61M 2205/6009; A61M 2210/1082; G16H 20/40; G16H 40/67; G16H 20/17; G16H 40/63; H04L 67/12; H04L 67/56
    See application file for complete search history.

(56) References Cited

U.S. PATENT DOCUMENTS

| | | | |
|---|---|---|---|
| 8,687,003 | B2 | 4/2014 | Dalesch et al. |
| 9,005,119 | B2 | 4/2015 | Iliff |
| 10,173,008 | B2 | 1/2019 | Simpson et al. |
| 10,780,224 | B2 | 9/2020 | Handler |
| 2002/0116226 | A1 | 8/2002 | Auer et al. |
| 2004/0068230 | A1 | 4/2004 | Estes |
| 2005/0277911 | A1 | 12/2005 | Stewart |
| 2006/0071797 | A1* | 4/2006 | Rosenfeld ............ G16H 40/67 600/300 |
| 2008/0208618 | A1* | 8/2008 | Schoenberg .......... G16H 40/63 705/2 |
| 2010/0021878 | A1 | 1/2010 | Kim et al. |
| 2012/0143116 | A1 | 6/2012 | Ware et al. |
| 2013/0090548 | A1 | 4/2013 | Hamilton et al. |
| 2013/0122528 | A1 | 5/2013 | Tyrell |
| 2014/0018727 | A1 | 1/2014 | Burbank et al. |
| 2016/0095976 | A1 | 4/2016 | Simpson et al. |
| 2019/0362455 | A1* | 11/2019 | Gajic .................... G16H 40/63 |

OTHER PUBLICATIONS

International Preliminary Report on Patentability for PCT/US2016/046818 dated Nov. 27, 2017—29 pages.

Critical Paths for Creating Data Platforms: Patient Safety: Intravenous Infusion Pump Devices, National Quality Forum, Oct. 31, 2012, 93 pages.

Driving healthcare intelligence throughout the continuum of care with standards-based interoperability, Philips Healthcare, Feb. 2012, 8 pages.

International Search Report for Application No. PCT/US16/46818 dated Jan. 26, 2017.

Japanese Patent Application No. 2018-507619 dated Feb. 19, 2019—5 pages.

Office Action dated Mar. 15, 2019—Colombian Application No. NC2018/0002319—7 pages.

Colombian Office Action dated Aug. 16, 2019—Appln. No. NC2018/0002319.

China Office Action Appln. No. 201680053306.0 dated Feb. 5, 2021—6 pages.

IPRP Appln. No. PCT/US2019/043450 dated Sep. 28, 2020—11 pages.

* cited by examiner

MEDICAL DEVICE DATA INTEGRATION APPARATUS AND METHODS

PRIORITY CLAIM

The present application is a continuation of U.S. patent application Ser. No. 17/027,098, filed Sep. 21, 2020, now U.S. Pat. No. 11,511,041, which is a continuation of U.S. patent application Ser. No. 16/679,803, filed Nov. 11, 2019, now U.S. Pat. No. 10,780,224, which is a continuation of U.S. patent application Ser. No. 16/126,366, filed Sep. 10, 2018, now U.S. Pat. No. 10,471,208, which is a divisional of U.S. patent application Ser. No. 15/235,701, filed Aug. 12, 2016, now U.S. Pat. No. 10,071,202, which claims priority to U.S. Provisional Patent Application No. 62/205,104, filed on Aug. 14, 2015, the entirety of which is incorporated herein by reference and relied upon.

BACKGROUND

Hospitals use different types of medical devices from different manufacturers. While the medical devices are configured to communicate over the same network (e.g., a local area network ("LAN")), the format of the data from each device is different. Each medical device developer may have their own proprietary format that is believed to be superior to other formats. Device developers attempt to gain widespread use of their proprietary data formats to restrict other developers from entering a hospital system or to obtain licensing payments from other developers that also desire to use the same data format. Even developers that use a standard data format, such as Health Level 7 ("HL7"), may still use customized data fields and definitions to make it difficult for other developers to integrate their medical devices into the same system.

In one example, a hospital system may select to use infusion pumps from a first developer. The data from the infusion pumps is formatted using a proprietary format. The use of the proprietary format forces the hospital to spend millions of dollars and months of time to develop an interface to enable the data from the infusion pumps to be compatible with the rest of the system. An interface may, for example, convert the infusion pump data into a format for inclusion within electronic medical records or transmission to user interface devices, such as a centralized monitoring system or clinician tablet computers/smartphones. The interface may also convert data originating in the hospital system into a format that is compatible with the infusion pump. For example, an electronic infusion therapy prescription from a pharmacy management system may be converted into a format that is recognized by an infusion pump.

As one can appreciate, the use of proprietary data formats and specialized interfaces make it difficult or almost impossible for medical devices to share or integrate data. This would require, for example, medical device developers to create separate interfaces for their devices that are compatible with every possible proprietary data format. Alternatively, the hospital system would have to create additional specialized interfaces. Given the number of different types of medical devices (e.g., infusion pumps, dialysis or renal therapy machines, physiological sensors/vital sign monitors, medical scanners, etc.), this is an almost impossible task.

SUMMARY

An example system, method, and apparatus are disclosed herein, which concurrently display data from different types of medical devices within a single display or user interface. The example system, method, and apparatus are configured with an integration engine that is specially programmed to convert data from multiple medical devices into a common format or protocol. The conversion of data from multiple devices into one format enables the data to be displayed concurrently within one user interface. The conversion of the data from multiple devices into one format also enables calculations or routines to be performed to determine relationships between the different types of data. For example, infusion data, renal failure therapy data, and urine collection data may be analyzed together to determine a patient's fluid balance. In other examples, the different types of data may be collectively analyzed to determine trends that may not be apparent by analyzing data from one medical device or sensor. Further, the integration of data from different devices enables the modification or adjustment of certain device limits or alarm limits.

Aspects of the subject matter described herein may be useful alone or in combination with one or more other aspect described herein. Without limiting the foregoing description, in a first aspect of the present disclosure, a networked healthcare system comprises a renal failure therapy machine communicatively coupled to a hospital information system configured to perform a renal failure therapy treatment for a patient, determine at least one renal failure therapy parameter related to the renal failure therapy treatment including an ultrafiltration rate at which fluid is removed from the patient, determine a renal failure therapy timestamp for the at least one renal failure therapy parameter, and transmit the at least one renal failure therapy parameter, a patient identifier of the patient, and the renal failure therapy timestamp to the hospital information system. The system also comprises an infusion pump communicatively coupled to the hospital information system configured to perform an infusion treatment for the same patient concurrently with the renal failure therapy machine, determine at least one infusion parameter related to the infusion treatment including an infusion rate at which fluid is infused into the patient, determine an infusion timestamp for the at least one infusion parameter, and transmit the at least one infusion parameter, the patient identifier, and the infusion timestamp to the hospital information system. The system further comprises a vital sign monitor associated with the patient communicatively coupled to the hospital information system, and operating in conjunction with an integration engine, configured to receive the at least one renal failure therapy parameter, the patient identifier, and the renal failure therapy timestamp, receive the at least one infusion parameter, the patient identifier, and the infusion timestamp, determine the at least one renal failure therapy parameter and the at least one infusion parameter are to be displayed at a combination user interface based on the patient identifier, determine a difference parameter based on a difference between the at least one infusion parameter and the at least one renal failure therapy parameter, display, within the combination user interface, the at least one renal failure therapy parameter within a renal failure therapy timeline, display, within the combination user interface, the at least one infusion parameter within an infusion timeline that is temporally aligned in parallel with the renal failure therapy timeline, and display, within the combination user interface, the difference parameter within a difference timeline that is temporally aligned in parallel with the renal failure therapy timeline and the infusion timeline.

In accordance with a second aspect of the present disclosure, which may be used in combination with any other aspect listed herein unless stated otherwise, the networked healthcare system further comprises a monitor gateway engine configured to receive the at least one renal failure therapy parameter, the patient identifier, and the renal failure therapy timestamp from the renal failure therapy machine, receive the at least one infusion parameter, the patient identifier, and the infusion timestamp from the infusion pump, determine the vital sign monitor among a plurality of vital sign monitors that is associated with the patient identifier, transmit the at least one renal failure therapy parameter, the patient identifier, and the renal failure therapy timestamp to the determined vital sign monitor, and transmit the at least one infusion parameter, the patient identifier, and the infusion timestamp to the determined vital sign monitor.

In accordance with a third aspect of the present disclosure, which may be used in combination with any other aspect listed herein unless stated otherwise, the networked healthcare system further comprises a renal failure therapy gateway engine configured to receive the at least one renal failure therapy parameter, the patient identifier, and the renal failure therapy timestamp from the renal failure therapy machine, determine the at least one renal failure therapy parameter, the patient identifier, and the renal failure therapy timestamp are to be transmitted to the monitor gateway engine, and transmit the at least one renal failure therapy parameter, the patient identifier, and the renal failure therapy timestamp to the monitor gateway engine.

In accordance with a fourth aspect of the present disclosure, which may be used in combination with any other aspect listed herein unless stated otherwise, the networked healthcare system further comprises an infusion gateway engine configured to receive the at least one infusion parameter, the patient identifier, and the infusion timestamp from the infusion pump, determine the at least one infusion parameter, the patient identifier, and the infusion timestamp are to be transmitted to the monitor gateway engine, and transmit the at least one infusion parameter, the patient identifier, and the infusion timestamp to the monitor gateway engine.

In accordance with a fifth aspect of the present disclosure, which may be used in combination with any other aspect listed herein unless stated otherwise, the vital sign monitor is communicatively coupled to a physiological sensor and configured to receive at least one physiological parameter from the physiological sensor and display, within the combination user interface, the at least one physiological parameter within a physiological timeline that is temporally aligned in parallel with the renal failure therapy timeline and the infusion timeline.

In accordance with a sixth aspect of the present disclosure, which may be used in combination with any other aspect listed herein unless stated otherwise, the vital sign monitor is configured to transmit the at least one physiological parameter to at least one of the renal failure therapy machine or the infusion pump via the monitor gateway engine.

In accordance with a seventh aspect of the present disclosure, which may be used in combination with any other aspect listed herein unless stated otherwise, the vital sign monitor is configured to display the at least one renal failure therapy parameter, the at least one infusion parameter, and the difference parameter as a numerical value adjacent to the respective timeline.

In accordance with an eighth aspect of the present disclosure, which may be used in combination with any other aspect listed herein unless stated otherwise, the infusion pump is a first infusion pump and the networked healthcare system further comprising a second infusion pump communicatively coupled to the hospital information system configured to perform a second infusion treatment for the same patient concurrently with the first infusion pump, determine at least one second infusion parameter related to the second infusion treatment including a second infusion rate at which a second fluid is infused into the patient, determine a second infusion timestamp for the at least one second infusion parameter, and transmit the at least one second infusion parameter, the patient identifier, and the second infusion timestamp to the hospital information system, wherein the vital sign monitor operating in conjunction with the integration engine is configured to receive the at least one second infusion parameter, the patient identifier, and the second infusion timestamp, determine the difference parameter based on a difference between the at least one infusion parameter, the at least one second infusion parameter, and the at least one renal failure therapy parameter, determine more than one infusion treatment is being provided to the patient, display, within the combination user interface, the at least one second infusion parameter within a second infusion timeline that is temporally aligned in parallel with the infusion timeline, and display, within the combination user interface, a first name of the fluid infused by the first infusion pump adjacent to the infusion timeline and a second name of the second fluid infused by the second infusion pump adjacent to the second infusion timeline.

In accordance with a ninth aspect of the present disclosure, which may be used in combination with any other aspect listed herein unless stated otherwise, the at least one difference parameter includes a net amount of fluid change within the patient per a time period.

In accordance with a tenth aspect of the present disclosure, which may be used in combination with any other aspect listed herein unless stated otherwise, the at least one renal failure therapy parameter includes a rate at which fluid is added to the patient from the renal failure therapy machine, a total amount of fluid removed from the patient, an amount of time remaining for the renal failure therapy treatment, and an event associated with the renal failure therapy treatment.

In accordance with an eleventh aspect of the present disclosure, which may be used in combination with any other aspect listed herein unless stated otherwise, the at least one infusion parameter includes a timestamp, a drug name of the fluid infused into the patient, a total amount of fluid infused into the patient, an amount of time remaining for the infusion treatment, an event associated with the infusion treatment, and a drug limit for the infusion treatment.

In accordance with a twelfth aspect of the present disclosure, which may be used in combination with any other aspect listed herein unless stated otherwise, a vital sign monitor apparatus comprises a renal failure therapy interface configured to receive at least one renal failure therapy parameter, a patient identifier, and a renal failure therapy timestamp from a renal failure therapy machine performing a renal failure therapy treatment for a patient associated with the patient identifier, an infusion pump interface configured to receive at least one infusion parameter, the patient identifier, and an infusion timestamp from an infusion pump performing an infusion treatment for the same patient, and a vital sign monitor engine communicatively coupled to the renal failure therapy interface and the infusion pump interface, the vital sign monitor engine configured to determine the at least one renal failure therapy parameter and the at least one infusion parameter are to be displayed in a combination user interface based on the patient identifier, display, within the combination user interface, the at least one renal failure therapy parameter within a renal failure therapy timeline, and display, within the combination user interface, the at least one infusion parameter within an infusion timeline that is temporally aligned in parallel with the renal failure therapy timeline.

In accordance with a thirteenth aspect of the present disclosure, which may be used in combination with any other aspect listed herein unless stated otherwise, an infusion pump apparatus comprises a renal failure therapy interface configured to receive at least one renal failure therapy parameter, a patient identifier and a renal failure therapy timestamp from a renal failure therapy machine performing a renal failure therapy treatment for a patient associated with the patient identifier, an infusion treatment processor configured to perform an infusion treatment for the same patient concurrently with the renal failure therapy machine, determine at least one infusion parameter related to the infusion treatment including an infusion rate at which fluid is infused into the patient, and determine an infusion timestamp for the at least one infusion parameter. The infusion pump apparatus also includes an infusion display engine configured to determine the at least one renal failure therapy parameter and the at least one infusion parameter are to be displayed at a combination user interface based on the patient identifier, determine a difference parameter based on a difference between the at least one infusion parameter and the at least one renal failure therapy parameter, display, within the combination user interface, the at least one renal failure therapy parameter within a renal failure therapy timeline, display, within the combination user interface, the at least one infusion parameter within an infusion timeline that is temporally aligned in parallel with the renal failure therapy timeline, and display, within the combination user interface, the difference parameter within a difference timeline that is temporally aligned in parallel with the renal failure therapy timeline and the infusion timeline.

In accordance with a fourteenth aspect of the present disclosure, which may be used in combination with any other aspect listed herein unless stated otherwise, a renal failure therapy machine apparatus comprises an infusion pump interface configured to receive at least one infusion parameter, a patient identifier, and an infusion timestamp from an infusion pump performing an infusion treatment for a patient associated with the patient identifier and a renal failure therapy treatment processor configured to perform a renal failure therapy treatment for the same patient concurrently with the infusion machine, determine at least one renal failure therapy parameter related to the renal failure therapy treatment including an ultrafiltration rate at which fluid is removed from the patient, and determine a renal failure therapy timestamp for the at least one infusion parameter. The renal failure therapy machine apparatus also includes a renal failure therapy display engine configured to determine the at least one renal failure therapy parameter and the at least one infusion parameter are to be displayed at a combination user interface based on the patient identifier, determine a difference parameter based on a difference between the at least one infusion parameter and the at least one renal failure therapy parameter, display, within the combination user interface, the at least one renal failure therapy parameter within a renal failure therapy timeline, display, within the combination user interface, the at least one infusion parameter within an infusion timeline that is temporally aligned in parallel with the renal failure therapy timeline, and display, within the combination user interface, the difference parameter within a difference timeline that is temporally aligned in parallel with the renal failure therapy timeline and the infusion timeline.

In accordance with a fifteenth aspect of the present disclosure, which may be used in combination with any other aspect listed herein unless stated otherwise, a hospital monitoring system apparatus comprises an infusion pump interface configured to receive at least one infusion parameter and a patient identifier from an infusion pump performing an infusion treatment for a patient associated with the patient identifier, a renal failure therapy interface configured to receive at least one renal failure therapy parameter and the patient identifier from a renal failure therapy machine performing a renal failure therapy treatment for the same patient, and a vital sign monitor interface configured to receive at least one physiological sensor parameter and the patient identifier from a vital sign monitor adjacent to the same patient. The hospital monitoring system apparatus also includes a monitoring system display engine configured to determine the at least one renal failure therapy parameter, the at least one infusion parameter, and the at least one physiological sensor parameter are to be displayed at a combination user interface based on the patient identifier, determine a difference parameter based on a difference between the at least one infusion parameter and the at least one renal failure therapy parameter, display, within the combination user interface, information related to the at least one renal failure therapy parameter, display, within the combination user interface, information related to the at least one infusion parameter, display, within the combination user interface, information related to the difference parameter, and display, within the combination user interface, information related to the at least one physiological sensor parameter.

In accordance with a sixteenth aspect of the present disclosure, any of the structure and functionality illustrated and described in connection with FIGS. 1 to 15 may be used in combination with any of the structure and functionality illustrated and described in connection with any of the other of FIGS. 1 to 15, and with any one or more of the preceding aspects unless stated otherwise.

Additional features and advantages of the disclosed system, method, and apparatus are described in, and will be apparent from, the following Detailed Description and the Figures.

DETAILED DESCRIPTION

Figure 1:
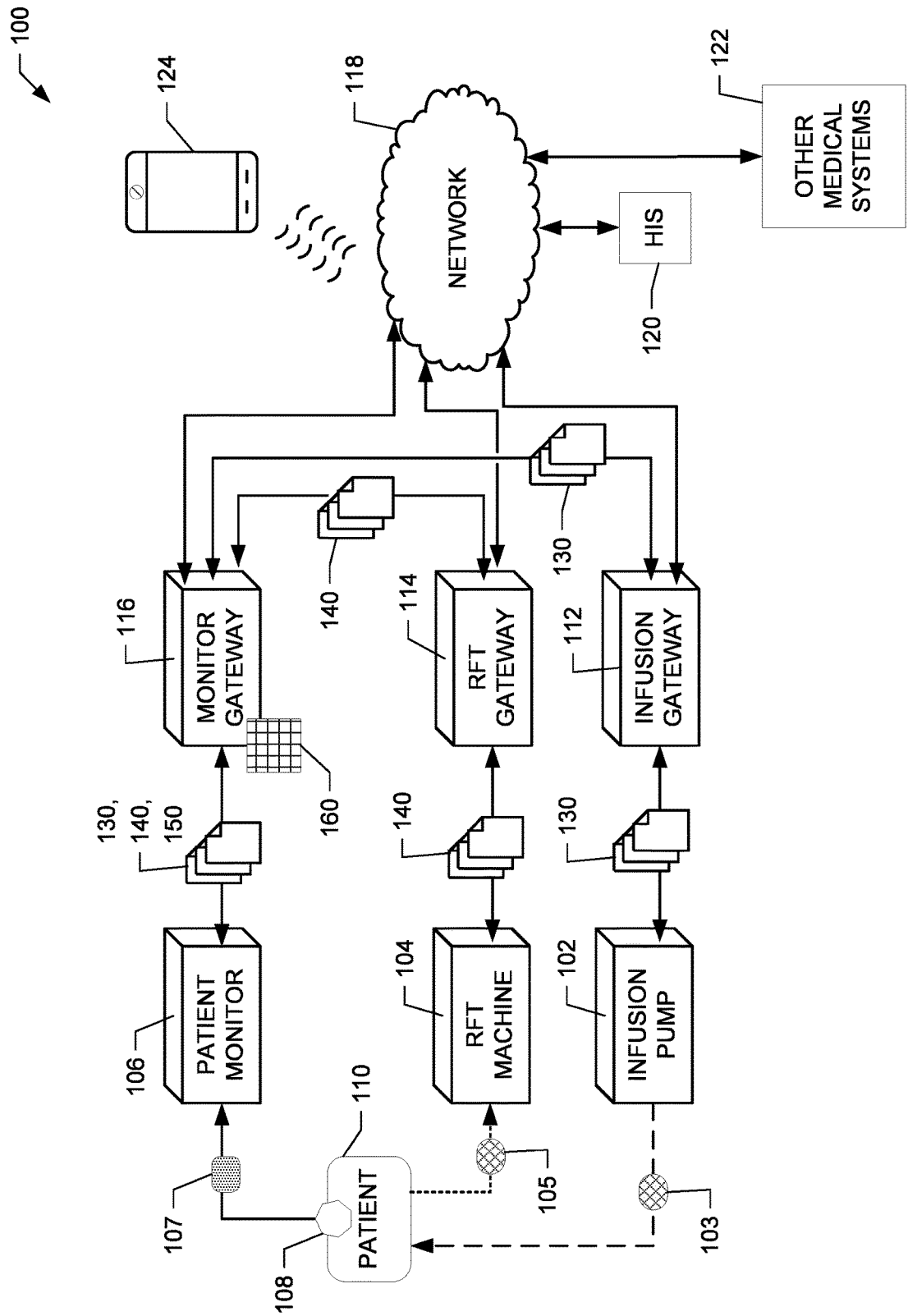
FIG. 1 shows a diagram of a hospital environment, according to an example embodiment of the present disclosure.

The present disclosure relates in general to a method, system, and apparatus to integrate and concurrently display data from different types of medical devices within a single display or user interface. The example method, system, and apparatus are configured to overcome known limitations of hospital systems by providing one module, referred to herein as an integration engine, which is configured to improve interoperability of medical devices by converting data from multiple formats, protocols, or standards into a single format. Despite the efforts of the Integrating the Healthcare Enterprise ("IHE") initiative and the Association for the Advancement of Medical Instrumentation ("AAMI") foundation, there are no national or worldwide standards for medical devices. For example, many infusion pump manufacturers have different standards or protocols for providing point-of-care infusion verification ("PIV"), device enterprise communication ("DEC"), patient identify binding ("PIB"), and alarm communication management ("ACM"). The result is that infusion data from different types of infusion pumps may have different ways in which the data, parameters, or fields are labeled. The differences may also include the types or units for labeling the data, how the data is time-stamped, or even how often the data is transmitted. Medical facilities accordingly typically have to either use medical devices from one provider (or a group of providers that use the same standard). These known systems are thereby limited in their ability to use data form multiple medical devices to construct an overall health assessment of a patient to provide dynamic device programming, programming limit adjustment, alarm limit adjustment, or even the concurrent display of data within a single display or user interface.

The example integration engine disclosed herein is configured as a module having multiple interfaces, which are each in turn configured to convert data from one standard or protocol into a common standard. The conversion of all the relevant medical data at the integration engine enables the integration engine to be programmed to analyze the different types of data to identify trends, determine differences or correlations, adjust limits/alarms, and/or adjust programming parameters, for example. In addition, the integration engine may be used in conjunction with a display device or monitor to visually provide the different types of medical data (and derivatives thereof) within one interface. The modularity of the integration engine enables interface updates to be provided easily and quickly as different medical devices are introduced into a system or as data standards or protocols change. Accordingly, the example integration engine improves overall system interoperability.

In an example, the integration engine is configured to combine infusion pump data with renal failure therapy data to enable a patient monitor to concurrently display the infusion pump data and renal failure therapy data. The example integration engine may also perform one or more calculations using the infusion and renal failure therapy data to determine a fluid balance. The integration engine may further integrate or incorporate the data into one or more algorithms or routines to concurrently display the data in conjunction with the calculated fluid balance or derived data to provide a more complete medical representation of the patient. The integration engine may also use the infusion pump data and the fluid balance derived data to adjust parameters of the renal failure therapy. Further, the integration engine may use the infusion pump data, renal failure therapy data, and/or the fluid balance derived data to provide an alarm when, for example, a fluid balance exceeds a specified threshold and/or when a renal failure therapy drain is not scheduled for a certain period of time.

As mentioned above, the example integration engine facilitates the display of different types of medical data, including derivatives, within one interface. As discussed herein, medical data incudes data from a medical device, including, for example, therapy progress data, programming instructions/parameters, operational parameters, status messages, alarms, alerts, etc. Medical data may also include physiological or other sensed data. In an example, medical data from an infusion pump includes an infusion rate, infusion dosage, infusion progress time, an operational status of the infusion pump (e.g., paused), a volume of fluid remaining to be infused, an indication of whether a drug library limit has been exceeded or overridden, pump alarms, pump alerts, and/or derivatives thereof.

As discussed herein, derivative data may include a combination of medical data received from one or more medical devices that is not determinative from any one stream of data alone. The combination may comprise, for example, adding, subtracting, or performing a specialized program or routine that incorporates medical data from one or more devices. Derivative data may also include an analysis that compares at least some medical data from one or more medical devices to data distributions. Derivative data may further include a result from performing a statistical analysis of medical data. In some instances, the integration engine may include one or more preconfigured or pre-stored algorithms or routines to determine derivative data. The preconfigured derivative data may correspond to most frequently used types of derivative data. In other examples, the example integration engine may enable a clinician to specify how derivative data is to be determined or generated from received medial data. It should be appreciated that disclosed conversion feature of the example integration engine facilitates the creation of derivative data from different types of medial data that may be generated in one or more different standards or protocols. This conversion feature enables data from many different devices and standards to be normalized or formatted into one standard or protocol (oftentimes compatible with the device displaying the data), which enables the multiple, different data streams to be compared, combined, integrated, or analyzed together. Under such a configuration, the integration engine enables the same calculations to be performed and data to be displayed regardless of the model or manufacturer of the medical devices and/or sensors.

FIG. 1 shows a diagram of a hospital environment 100 configured to implement the example methods, apparatus, and system described herein, according to an example embodiment of the present disclosure. The example environment 100 includes medical devices such as, for example, an infusion pump 102, a dialysis or renal failure therapy ("RFT") machine 104, a patient monitor 106, and/or one or more physiological sensors 108 (e.g., vital sign sensors). It should be appreciated that the example hospital environment 100 may include other types of medical devices and/or a plurality of pumps 102, RFT machines 104, monitors 106, and/or sensors 108. Collectively, the medical devices are configured to provide a therapy to a patient 110, read a physiological parameter or vital sign from the patient, and/or display data regarding the patient or treatment.

The example environment 100 also includes an infusion gateway 112, a RFT gateway 114, and a monitor gateway 116. In alternative embodiments, the gateways 112, 114, and 116 may be combined into a single gateway. In other alternative embodiments, the gateways 112, 114, and 116 may be combined with the respective medical device 102, 104, and 106. As illustrated in FIG. 1, the infusion gateway 112 and the RFT gateway 114 are communicatively coupled to the monitor gateway 116 via a hardwired connection and/or a wireless connection (e.g., an Ethernet network, LAN, WLAN, etc.). The gateways 112, 114, and 116 are each communicatively coupled to a network 118, which may include the same Ethernet network, LAN, WLAN and/or in addition to an external network such as the Internet. The network 118 is communicatively coupled to a hospital information system ("HIS") 120, one or more medical networks 122, and/or one or more clinician devices 124.

The example infusion pump 102 may include any pump capable of delivering an intravenous therapy to the patient 110 via one or more line sets. Examples include a syringe pump, a linear peristaltic pump, a large volume pump ("LVP"), an ambulatory pump, multi-channel pump, etc. A syringe pump uses a motor connected to a drive arm to actuate a plunger within a syringe. A linear peristaltic pump uses a rotor to compress part of a tube while rotating. Oftentimes, one or more rollers of the rotor contact the tube for half a rotation. The compressed rotation causes a defined amount of fluid to pass through the tube. LVPs typically use one or more fingers or arms to compress a portion of intravenous therapy ("IV") tube. The timing of the finger actuation on the tube causes constant or near constant movement of a fluid through the tube.

Figure 2:
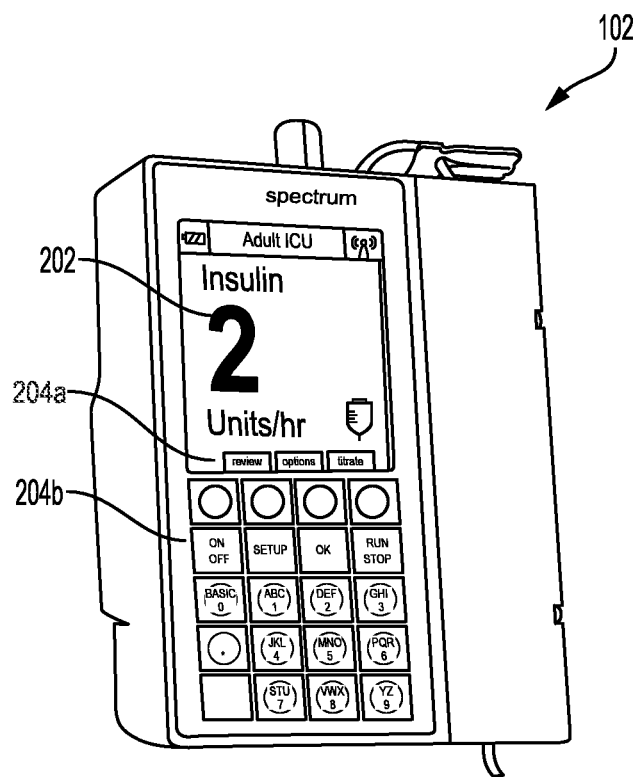
FIG. 2 shows a diagram of an example infusion pump comprising the Baxter® SIGMA Spectrum pump, which may be implemented within the hospital environment of FIG. 1, according to an example embodiment of the present disclosure.

FIG. 2 shows a diagram of an example infusion pump 102 including the Baxter® SIGMA Spectrum™ pump, according to an example embodiment of the present disclosure. The example infusion pump 102 of FIG. 2 includes a display 202 with interfaces 204a and 204b to enable a clinician to specify or program an infusion therapy. Other examples of infusion pumps include a linear volume parenteral pump described in U.S. Publication No. 2013/0336814, a syringe pump described in U.S. Publication No. 2015/0157791, an ambulatory infusion pump described in U.S. Pat. No. 7,059,840, an infusion pump described in U.S. Pat. No. 5,395,320, and an infusion pump described in U.S. Pat. No. 5,764,034, the entirety of each are incorporated herein by reference. The infusion pump 102 may also include the Baxter® Colleague™ volumetric infusion pump.

Returning to FIG. 1, the infusion pump 102 may be configured to receive electronic prescriptions (or software updates) from the HIS 120 or other pharmacy system via the infusion gateway 112. For example, the gateway 112 may send an electronic prescription (or software update) to the infusion pump 102 at a predetermined time and/or when the infusion pump 102 is available to accept the prescription. In other instances, the infusion pump 102 may be configured to periodically poll the gateway 112 to determine if an electronic prescription (or software update) is awaiting to be downloaded to the pump. The infusion pump 102 may include a memory storing one or more drug libraries that include particular program parameter limits based on care area, dose change, rate of change, drug type, concentration, patient age, patient weight, etc. The limits are configured to ensure that a received prescription or entered infusion therapy is within acceptable ranges and/or limits decided by a medical facility, doctor, or clinician.

The infusion pump 102 is configured to perform an infusion therapy on the patient 110, which includes infusion of one or more solutions 103 or drugs into the patient. The infusion pump 102 operates according to an infusion prescription entered by a clinician at a user interface of the pump (e.g., the interface 204 of FIG. 2) or received via the infusion gateway 112. The infusion pump 102 may compare the prescription to the drug library and provide any alerts or alarms if a parameter of the prescription violates a soft or hard limit. The infusion pump 102 is configured to monitor the progress of the therapy and periodically transmit infusion therapy progress data 130 to the gateway 112. The therapy progress data 130, as disclosed herein, may include, for example, an infusion rate, dose, a total volume infused, a time remaining for the therapy, drug concentration, rate change, a volume remaining within a medication container, a drug name, a patient identifier, titration information, bolus information, a care area identifier, a timestamp when the data was generated, an alarm condition, an alert condition, an event, etc. The infusion pump 102 may transmit the data continuously, periodically (e.g., every 30 seconds, 1 minute, etc.), or upon request by the gateway 112.

The infusion gateway 112 of FIG. 1 includes a server, processor, computer, etc. configured to communicate with the infusion pump 102. The infusion gateway 112 may include, for example, the Baxter® CareEverywhere gateway. In some embodiments, the gateway 112 may be communicatively coupled to more than one infusion pump. The infusion gateway 112 is configured to provide bi-directional communication with the pump 102 for the wired/wireless secure transfer for drug libraries, infusion prescriptions, and therapy progress data 130. The gateway 112 may also be configured to integrate with the HIS 120 or other hospital system to facilitate the transmission of the infusion therapy progress data 130 from the pump 102 to, for example, a hospital electronic medical record ("EMR").

The HIS 120 of FIG. 1 is a network system configured in a client-server architecture to facilitate the transmission of medical data, including the data 130, 140, and 150 among different medical systems. The HIS 120 may include one or more servers configured to process or store medical data. The HIS 120 may also include one or more servers for analyzing medical data or receiving medical data from other portions of the hospital environment 100. The HIS 120 may include, for example a server for managing medical data storage to EMRs. The HIS 120 may use a patient identifier, or similar, to determine which EMR is to receive medical data for storage. The HIS 120 may also include or be communicatively coupled to a laboratory information system, pharmacy system, a policy/procedure management system, or a continuous quality improvement ("CQI") system. The laboratory system is configured to generate medical data based on analysis of patient biological samples. The pharmacy system is configured to generate medical prescriptions for a patient, including instructions for programming the infusion pump 102 and/or the RFT machine 104. The policy/procedure management system is configured to manage drug libraries and/or thresholds for alarms/alerts. The CQI system is configured to generate statistical and/or analytical reports based on, for example, infusion therapy progress data 130 from one or more patients. The HIS 120 may also include or be connected to one or more monitors configured to display at least a portion of the infusion therapy progress data 130. The HIS 120 may further integrate the infusion therapy progress data 130, renal failure therapy progress data 140, and/or physiological data 150 into clinician documentation to provide quick and accurate infusion pump documentation and access to near real-time trends, and contextual patient infusion data that improves patient treatment.

The example RFT machine 104 of FIG. 1 may include any hemodialysis, hemofiltration, hemodiafiltration, continuous renal replacement therapy ("CRRT"), or peritoneal dialysis ("PD") machine. The patient 110, undergoing a renal failure therapy, for example, is connected to the RFT machine 104, where the patient's blood may be pumped through the machine. The blood passes through a dialyzer of the machine 104, which removes waste, toxins and excess water from the blood. The cleaned blood is returned to the patient. In PD, treatment fluid is delivered to and removed from a patient's peritoneal cavity to remove toxins and excess water.

Figure 3:
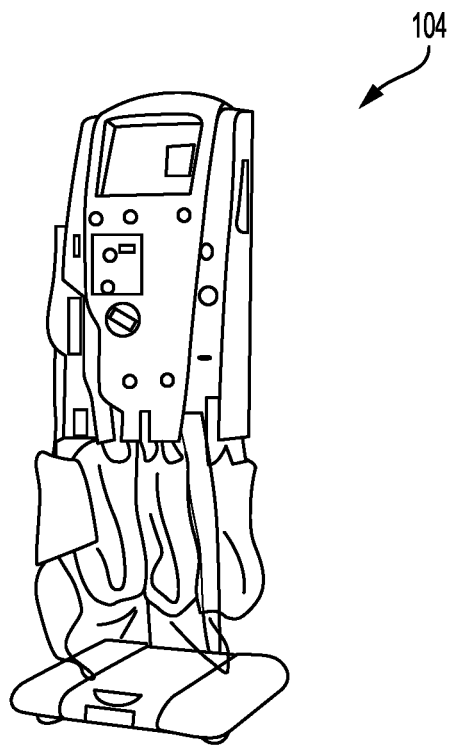
FIG. 3 shows a diagram of an example dialysis or renal failure therapy machine comprising the Gambro® Prismaflex® CRRT machine, which may be implemented within the hospital environment of FIG. 1, according to an example embodiment of the present disclosure.

FIG. 3 shows a diagram of an example RFT machine 104 comprising the Gambro® Prismaflex® CRRT machine, according to an example embodiment of the present disclosure. Other examples of RFT machines 104 include a peritoneal dialysis machine described in U.S. Pat. No. 8,403,880, a hemodialysis dialysis machine described in U.S. Publication No. 2014/0112828, and a peritoneal dialysis machine described in U.S. Publication No. 2011/0106002, the entirety of each are incorporated herein by reference.

CRRT is a dialysis modality typically used to treat emergency or critically ill, hospitalized patients in an intensive care unit who develop acute kidney injury ("AKI"). Unlike chronic kidney disease, which occurs slowly over time, AKI often occurs in hospitalized patients and typically occurs over a few hours to a few days.

Hemodialysis is a renal failure treatment in which waste from the blood is diffused across a semi-permeable membrane. During hemodialysis, blood is removed from the patient and flows through a semi-permeable membrane assembly (dialyzer), where the blood flows generally counter-current to dialysis solution flowing on the other side of the semipermeable membrane. In the dialyzer, toxins from the blood travel across the semi-permeable membrane and exit the dialyzer into used dialysis solution (dialysate). The cleaned blood, having flowed through the dialyzer, is then returned to the patient.

In the dialyzer, a pressure differential is created across the semi-permeable membrane by removing dialysate at a flow rate that is greater than that used to introduce the dialysis solution into the dialyzer. This pressure differential pulls fluid containing small, middle, and large molecule toxins across the semi-permeable membrane. Flow and volume measurements are used to control the amount of fluid (ultrafiltration) that is removed. As illustrated above, a hemodialysis machine's pump typically pulls blood from the arterial side of the patient, pushes it into and through the dialyzer, and through a drip chamber that separates out air, before returning the dialyzed blood to the venous side of the patient.

The RFT machine 104 can alternatively be a hemofiltration machine. Hemofiltration is another renal failure treatment, similar to hemodialysis. During hemofiltration, a patient's blood is also passed through a semipermeable membrane (a hemofilter), wherein fluid (including waste products) is pulled across the semipermeable membrane by a pressure differential. This convective flow brings certain sizes of molecular toxins and electrolytes (which are difficult for hemodialysis to clean) across the semipermeable membrane. During hemofiltration, a replacement fluid is added to the blood to replace fluid volume and electrolytes removed from the blood through the hemofilter. Hemofiltration in which replacement fluid is added to the blood prior to the hemofilter is known as pre-dilution hemofiltration. Hemofiltration in which replacement fluid is added to the blood after the hemofilter is known as post-dilution hemofiltration.

The RFT machine 104 can alternatively be a hemodiafiltration machine. Hemodiafiltration is a further renal failure treatment that uses hemodialysis in combination with hemofiltration. Blood is pumped through a dialyzer, which accepts fresh dialysis fluid, unlike a hemofilter. With hemodiafiltration, however, replacement fluid is delivered to the blood circuit, similar to hemofiltration. Hemodiafiltration is accordingly a neighbor of hemodialysis and hemofiltration.

The RFT machine 104 can alternatively be a peritoneal dialysis machine. Peritoneal dialysis uses a dialysis solution, also called dialysate, which is infused into a patient's peritoneal cavity via a catheter. The dialysate contacts the peritoneal membrane of the patient's peritoneal cavity. Waste, toxins and excess water pass from the patient's bloodstream, through the peritoneal membrane and into the dialysate due an osmotic gradient created by the solution. Spent dialysate 105 is drained from the patient, removing waste, toxins and excess water from the patient. This cycle is repeated.

An example peritoneal dialysis machine, operating as the RFT machine 104 of FIG. 1, may perform various types of additional peritoneal dialysis therapies, including continuous cycling peritoneal dialysis ("CCPD"), tidal flow automated peritoneal dialysis ("APD"), and continuous flow peritoneal dialysis ("CFPD"). APD machines perform drain, fill, and dwell cycles automatically, typically while the patient sleeps. APD machines free patients or clinicians from having to manually perform the treatment cycles and from having to transport supplies during the day. APD machines connect fluidly to an implanted catheter, a source or bag of fresh dialysate, and a fluid drain. APD machines pump fresh dialysate from a dialysate source, through the catheter, into the patient's peritoneal cavity. APD machines allow the dialysate to dwell within the cavity, thereby enabling the transfer of waste, toxins and excess water to take place. The source can be multiple sterile dialysate solution bags. APD machines pump spent dialysate from the peritoneal cavity, though the catheter, to the drain. As with the manual process, several drain, fill and dwell cycles occur during APD. A "last fill" occurs at the end of CAPD and APD, which remains in the peritoneal cavity of the patient until the next treatment.

CCPD treatments attempt to drain the patient fully upon each drain. CCPD and/or APD may be batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Peritoneal dialysis dialysate may include a solution or mixture that includes between 0.5% and 10% dextrose (or more generally glucose), preferably between 1.5% and 4.25%. Peritoneal dialysis dialysate may include, for example, Dianeal®, Physioneal®, Nutrineal®, and Extraneal® dialysates marketed by the assignee of the present disclosure. The dialysate may additionally or alternatively include a percentage of icodextrin. It should be appreciated that in some embodiments of the present disclosure, the dialysate may be infused into the patient 110 via the infusion pump 102 rather than the RFT machine 104.

Continuous flow, or CFPD, dialysis systems clean or regenerate spent dialysate instead of discarding it. CFPD systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia (e.g. ammonium cation). The ammonia is then removed from the dialysate by adsorption prior to reintroduction of the dialysate into the peritoneal cavity. Additional sensors are employed to monitor the removal of ammonia. CFPD systems are typically more complicated than batch systems.

In both hemodialysis and peritoneal dialysis, "sorbent" technology can be used to remove uremic toxins from waste dialysate, re-inject therapeutic agents (such as ions and/or glucose) into the treated fluid, and reuse that fluid to continue the dialysis of the patient. One commonly used sorbent is made from zirconium phosphate, which is used to remove ammonia generated from the hydrolysis of urea. Typically, a large quantity of sorbent is necessary to remove the ammonia generated during dialysis treatments.

Similar to the infusion pump 102, the RFT machine 104 may be programmed locally with a dialysis prescription or receive a dialysis prescription via the RFT gateway 114. The RFT machine 104 is configured to perform a renal failure therapy on the patient 110, which, as discussed above, includes removing ultrafiltration from the patient 110. With peritoneal dialysis, the RFT machine 104 infuses dialysate into the patient 110 during the fill cycles. For any dialysis prescription, the RFT machine 104 may compare parameters of the prescription to one or more limits and provide any alerts or alarms if a parameter of the prescription violates a soft or hard limit. The RFT machine 104 is configured to monitor the progress of the therapy and periodically transmit renal failure therapy progress data 140 to the RFT gateway 114. The renal failure therapy progress data 140 may include, for example, a fill rate, a dwell time, a drain or fluid removal rate, a blood flow rate, effluent dose, an ultrafiltration removal rate, a dialysate removal rate, a total dialysate infused, dialysate flow, replacement pre-flow, replacement post-flow, patient weight balance, return pressure, excess patient fluid sign, filtration fraction, a time remaining, dialysate concentration, dialysate name, a patient identifier, a room identifier, a care area identifier, a timestamp when the data was generated, an alarm condition, an alert condition, an event, etc. The RFT machine 104 may transmit the data continuously, periodically (e.g., every 30 seconds, 1 minutes, etc.), or upon request by the RFT gateway 114.

The RFT gateway 114 includes a server, processor, computer, etc. configured to communicate with the RFT machine 104. The RFT gateway 114 may include, for example, the Global Baxter Exchange™ ("GBX") server or gateway. The gateway 114 may be communicatively coupled to more than one RFT machine. The RFT gateway 114 is configured to provide bi-directional communication with the machine 104 for the wired/wireless secure transfer of drug libraries, dialysis prescriptions, and renal failure therapy progress data 140. The gateway 114 may also be configured to integrate with or communicate with the HIS 120 or other hospital system to transmit the renal failure therapy progress data 140 from the RFT machine 104 to a patient's EMR. The renal failure therapy progress data 140 may also be used by the HIS 120 for analytics, reporting, and/or consulting.

The example patient monitor 106 of the illustrated embodiment of FIG. 1 is configured to display one or more graphs of physiological data 107 from the physiological sensor 108. The monitor 106 may be wired or wirelessly coupled to the sensor 108, which may include, for example, a heart rate sensor (e.g., an EKG sensor, an ECG sensor), a temperature sensor, a pulse oximetry sensor, a patient weight scale, a glucose sensor, a respiratory sensor, a blood pressure sensor, etc. The patient monitor 106 is configured to display the data from the sensors within a time-based graph. The patient monitor 106 may also display a numerical value of the most recent data from the sensor 108 in addition to color coding the data. Collectively, the data received at the patient monitor 106 from the sensors 108 may be referred to herein as physiological data 150.

The patient monitor 106 is communicatively coupled to the monitor gateway 116. The patient monitor 106 may continuously, periodically, or upon request, transmit the physiological data 150 to the monitor gateway 116, which may then transmit the physiological data 150 to the HIS 120 for inclusion in the patient's EMR or within a clinician's records. The physiological data 150 may also be used with the data 130 and 140 within a CQI system or transmitted to the clinician device 124.

The example monitor gateway 116 of FIG. 1 includes an integration engine 160 configured to process the data 130, 140, and 150 respectively from the infusion pump 102, the RFT machine 104, and the patient monitor 106. The example integration engine 160 is configured to analyze the data 130, 140, and 150 in conjunction with one or more routines, algorithms, etc. to determine how the data is to be displayed and/or presented. For instance, while the patient monitor 106 is configured to display the physiological data 150 from connected sensors 108, the patient monitor 106 may not be configured to display the data 130 and 140. In some embodiments, the data 130 and 140 may be in a standard or format that is not compatible or recognized by the patient monitor 106

The integration engine 160 is configured to convert or otherwise format the data 130 and 140 into a standard, format, or protocol that is compatible with the monitor 106 (e.g., referred to herein as a common format). The integration engine 160 is also configured to determine which of the infusion data 130 and dialysis data 140 is to be displayed at a particular time and instruct the monitor 106 to display the converted or formatted data in conjunction with the physiological data 150 at the specified time. The result is the concurrent display of infusion data and renal failure therapy data with physiological data from the same time. Such a configuration enables a clinician to view in one location infusion data, renal failure therapy data, and physiological data, and be able to quickly determine how a change to the renal failure therapy or infusion affects a patient's physiological condition.

The concurrent processing, integration, and conversion of the data 130, 140 and/or 150 enables the integration engine

160 to also determine conditions, deltas, or derivatives based on the different types of data. For example, the integration engine 160 may include a routine that compares an amount of fluid infused into a patient to fluid removed from the patient through dialysis or a renal failure therapy to determine derivative data indicative of fluid balance. The integration engine 160 may then calculate a new fluid difference and provide this information to the monitor 106 for concurrent viewing with the infusion and renal failure therapy data 140.

Such a configuration also enables the integration engine 160 to provide enhanced alerts and/or alarms. For example, the integration engine 160 may be configured to operate a routine that compares the patient's physiological parameters to hard limits, soft limits, or delta limits. The integration engine 160 may also analyze the therapy progress data 130 and/or renal failure therapy data 140 in conjunction with one or more limits. In one example, the integration engine 160 may detect that a patient's physiological parameters are trending to a dangerous level and activate an alarm to change (or stop) the infusion therapy or renal failure therapy. In another example, the integration engine 160 may detect that a physiological condition is approaching a first limit. However, the integration engine 160 also determines that an infusion is occurring and that a second higher limit should be used instead.

It should be appreciated that having access to different types of data 130, 140, and 150 enables the integration engine 160 to provide countless improvements for interoperability and patient care. The integration engine 160 may be configured to dynamically adjust medical device operational limits and/or alarm/alert thresholds based on certain of the data 130, 140, and 150 (and/or derivatives thereof). For instance, the infusion pump 102 typically includes one or more drug libraries that define operational parameter limits based on patient weight, gender, care area, etc. The use of the integration engine 160 enables at least one of the limits to be specified by routines or algorithms based on certain data. For example, an infusion dosage limit may be adjusted based on a type of renal failure therapy being provided concurrently. In other examples, the integration engine 160 may adjust prescription settings based on analysis of the data 130, 140, and/or 150 (and derivatives thereof). For instance, an infusion rate may be decreased (according to a specified routine) if renal failure therapy progress data 140 indicatives that the patient 110 is accumulating too much fluid. To change a limit or operational parameter, the integration engine 160 may be configured to create instructions in a message standard appropriate for the infusion pump 102 to cause the limits or operational parameters to be adjusted.

The example integration engine 160 may also facilitate the use of alarms and/or alerts with dynamic triggering conditions and/or thresholds. For instance, the integration engine may analyze the data 130, 140, and/or 150 (and derivatives thereof) to determine if certain thresholds for alarms/alerts of the infusion pump 102 and/or the RFT machine 104 are to be adjusted. Responsive to detecting that a threshold is to be changed, the integration engine 160 transmits one or more messages to the appropriate device 102 or 104 indicative of the threshold modification. The integration engine 160 is configured to use one or more algorithms and/or routines to determine how combinations of the data 130, 140, and/or 150 (and derivatives thereof) affect alarm/alert thresholds.

The example integration engine 160 may also be configured to generate its own alerts and/or alarms based on the data 130, 140, and/or 150 (and derivatives thereof). The integration engine 160 may include a list or table of alarms/alerts and corresponding threshold conditions. The integration engine compares the appropriate data 130, 140, and/or 150 (and derivatives thereof) to the lists to determine if an alarm or alert is to be generated. The table may also specify a destination to where the alarm/alert is to be transmitted. For instance, alarms/alerts may be transmitted for display or audio actuation on the infusion pump 102, the RFT machine 104, and/or the patient monitor 106. Additionally or alternatively, the integration engine 160 may transmit alarms/alerts to the HIS 120 or other medical systems 122. Such a configuration enables, for example, alarms or alerts to be generated based on combinations of the therapy progress data 130, the renal failure therapy progress data 140, the physiological data 150, and/or derivatives thereof. For example, the integration engine 160 may generate an alarm when a fluid balance (which is derived from infusion and RFT data) exceeds a threshold. Further, the integration engine 160 may be configured to adjust conditions and/or thresholds for the alarms/limits.

In some instances, the integration engine 160 may provide programming instructions in combination with (or in response to) the alarms and/or alerts. For example, the integration engine 160 may determine an issue with the infusion pump 102 (or receive an alarm from the infusion pump 102) and determine, using a routine to analyze the data, that the RFT machine 104 is to be suspended. The integration engine 160 accordingly transmits one or more messages, in a standard appropriate for the RFT machine 104, to the RFT machine 104, causing the RFT machine 104 to suspend operation.

In some embodiments, the integration engine 160 may be included within a computer, processor, and/or server that is communicatively coupled to the monitor gateway 116. Alternatively, the integration engine 160 may be distributed among a computer, the monitor gateway 116, and the patient monitor 106. Such configurations enable a clinician to modify or select (from a computer or smartphone) which data is to be displayed and which routines are to be used for processing the data 130, 140, and 150. The selection by the clinician may update how the monitor gateway 116 routes and/or processes the data and/or how the patient monitor 106 processes data. Such a configuration also enables user interface functionality to be included in conjunction with the data. This may include providing a clinician the ability to select a net amount of fluid waveform or to see individual waveforms of the data 130, 140, and 150 that contribute to the determined amount.

In some embodiments, the infusion pump 102 and/or the RFT machine 104 may also be communicatively coupled to one or more physiological sensors 108. For example, the infusion pump 102 may be connected to a pulse oximetry sensor. The infusion pump 102 may be configured to integrate or otherwise include data from the pulse oximetry sensor into the infusion therapy progress data 130 or, alternatively, transmit the pulse oximetry data separately to the infusion gateway 112. Similarly, the RFT machine 104 may be communicatively coupled to a blood pressure sensor, a patient weight scale, a glucose sensor, a cardiac monitor, etc. The RFT machine 104 may be configured to integrate or otherwise include data from the sensors into the renal failure therapy progress data 140 or, alternatively, transmit the sensor data separately to the RFT gateway 114.

Example Embodiment

It should be appreciated that monitoring a patient's fluid balance is important to prevent dehydration or overhydration. However, known fluid balance recording systems are notorious for being inadequate or inaccurate because these systems require separate collection and input of infusion and renal failure therapy information. However, a clinician may not timely record renal failure therapy or infusion information or may record one but not the other. In some instances, the clinician may spend some time recording the infusion information and then the renal failure therapy information. However, the difference in time between collecting the infusion and renal failure therapy information may produce correlation errors.

In the example hospital environment 100 of FIG. 1, the infusion pump 102 is pumping or infusing fluid into the patient 110, while the RFT machine 104 removes fluid 105 from the patient 110. The RFT machine 104 may also be filling the patient 110 with fluid. In an example, the infusion pump 102 may infuse one or more medications or saline, while the RFT machine 104 is configured to perform hemodialysis or peritoneal dialysis. Such a configuration may be used for certain medications that need to be removed quickly after being infused or in situations where medications are administered to patients with kidney failure.

The fluid 'ins and outs' are a key aspect of determining and managing a patient's fluid and hemodynamic status. Before treatment begins, the gateways 112, 114, and 116 are configured to route and process data so that all data related to the patient 110 is aggregated such that at least some of the aggregated data may be integrated and/or processed and displayed. In this instance, the patient monitor 106 may receive or otherwise obtain an identifier of the patient 110. For instance, a bar code scanner attached to the monitor 106 may be used to scan a wristband of the patient 110. The monitor 106 may then transmit the identifier in addition to an IP address or MAC address of the monitor 106 to the gateway 116, where the integration engine 160 correlates the address of the monitor 106 with the patient identifier.

Also before treatment, the infusion pump 102 and the RFT machine 104 may obtain or otherwise receive an identifier of the patient. For instance, a bar code scanner built into the infusion pump or communicatively coupled to the infusion pump may scan the patient's wristband or a medication container to obtain the patient's identifier. The infusion pump 102 and the RFT machine 104 include the patient's identifier within the data 130 and 140.

During treatment, the infusion pump 102 generates the infusion therapy progress data 130, which is transmitted to the gateway 112, while and the RFT machine generates the renal failure therapy progress data 140, which is transmitted to the gateway 114. The example gateways 112 and 114 transmit the respective data to the monitor gateway 116. The example patient monitor 106 also transmits the physiological data 150 (including the patient identifier) to the monitor gateway 106. The integration engine 160 at the monitor gateway 106 analyzes the data 130 and 140 for the patient identifier. All of the data with the same patient identifier is then processed by the integration engine 160 for display at the patient monitor 106. For instance, the integration engine 160 may search all of the data associated with the same patient for timestamp information. The integration engine 160 may then send the data with the same timestamps to the patient monitor 106 for display within respective charts.

The example integration engine 160 may also calculate or process the data 130, 140, and 150 for specific derivative values or parameters. For instance, the integration engine 160 may use a rate of infusion from the infusion pump 102 and a dialysis fluid removal rate from the RFT machine 104 to determine a net fluid accumulation in the patient 110. The integration engine 160 may then attach a timestamp to the net fluid accumulation data corresponding to the timestamp of the rate of infusion and the dialysis fluid removal rate. The integration engine 160 then sends the net fluid accumulation data, the rate of infusion, and the dialysis fluid removal rate to the monitor 106 for display.

Figure 4:
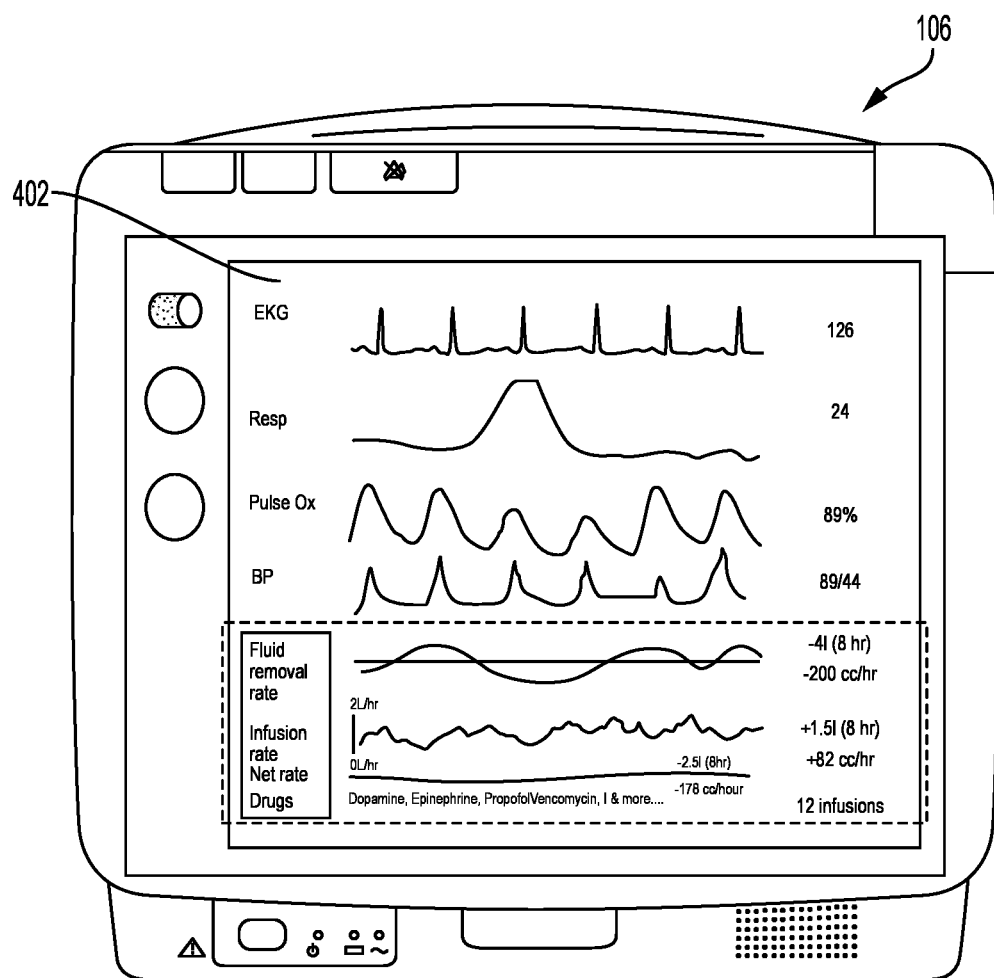
FIG. 4 shows a diagram of a patient monitor displaying data from an integration engine within the hospital environment of FIG. 1, according to an example embodiment of the present disclosure.

FIG. 4 shows a diagram of the patient monitor 106 displaying data from the integration engine 160, according to an example embodiment of the present disclosure. A user interface 402 is configured to display physiological sensor data 150 including, for example, EKG data, respiratory data, pulse oximetry data, and blood pressure data. In conjunction with the most recent value, the user interface 402 displays a timeline or chart of each data type. It should be appreciated that the timeline scale for each data type may be the same, but could be different based on user selections.

The user interface 402 also shows a numerical value illustrating an amount of fluid per time period (cc/hour) actively being infused into the patient 110 via the infusion pump 102. The integration engine 160 may combine data from all infusion pumps 102 connected to the patient 110 and/or data from the RFT machine 104. The integration engine 160 may further combine fluid input from other devices such as, for example, nutritional feeding tubes. The data is displayed as a waveform of input rate over recent time in addition to a numerical value showing a total fluid infused over some configurable recent time period (e.g., last 8 hours).

The user interface 402 further shows a numerical value illustrating an amount of fluid per time period (cc/hour) actively being removed from the patient 110 via the RFT machine 104. The integration engine 160 may combine data from all RFT machines 104 connected to the patient 110 and/or data from a urine collection device (e.g., the physiological sensor 108). The data is displayed as a waveform of output rate over recent time in addition to a numerical value showing a total fluid removed over some configurable recent time period (e.g., last 8 hours).

The example user interface 402 moreover shows a numerical value illustrating the net amount of fluid change per time period (e.g., cc/hour). This derivative data is displayed as a waveform of net rate over recent time in addition to a numerical value showing a net fluid change over some configurable recent time period (e.g., last 8 hours).

The example integration engine 160 may also be configured to send instructions to the monitor 106 regarding which data is to be displayed. For example, the integration engine 160 may only receive the data 130 from the infusion pump 102. In response, the integration engine 160 may send an instruction to the monitor 106 indicating that only a timeline or waveform for infusion rate is to be displayed.

As discussed above, more than one infusion pump 102 may be connected to the patient 110. In these circumstances, the integration engine 160 may aggregate (according to a predefined routine) the fluid input to the patient based on the data 130 from all of the pumps. In addition, the integration engine 160 may be configured to create a list or data structure of the names of the substances being infused into the patient. The integration engine 160 may order the names of the various substances and send the order to the monitor 106 for display within user interface 402. The integration engine 106 may order the names based on importance, criticality to the patient, infusion rate, etc. In instances where the number of names is greater than a display area within the user interface 402, the example integration engine 160 may specify which names are to be displayed and which names are to be hidden behind an ellipsis. The integration engine 160 may set the ellipsis as an input field, such that, selection by the user causes the monitor 106 to display the other names, or causes the integration engine 160 to send the other names.

The integration engine 160 may also determine which infusions are active compared to infusions that are paused or finished (based on status indicators or infusion rate information specified within the infusion therapy progress data 130). The integration engine 160 may order the infusion names based on activity and/or may color code the names based on activity. In some instances, the integration engine 160 may cause the monitor 106 to display, adjacent to the net amount of fluid waveform, an indication of the active infusions.

In some instances, each of the names may also be set as an input field. Selection of a particular name may cause the integration engine 160 to display fluid input to the patient for only that selected substance. The integration engine 160 may also determine for display a net amount of fluid between the selected infusion substance the dialysis data. The integration engine 160 may be configured to perform this net amount of fluid input for multiple selections of infusion substances that comprise a subset of the entire set of known infusion substances.

It should be appreciated that the integration engine 160 may include a limitless number of routines specifying how the data 130, 140, and 150 (and derivatives thereof) is to be processed and configured for display. Some of the routines may be predefined based on defined relationships between the data. Other ones of the routines may be specified by an operator at the monitor 106. For example, a clinician may select which data types are to be displayed at the monitor 106. The selection of certain data types may cause the integration engine 160 to execute a routine to determine the selected data type.

The example integration engine 160 also is configured to ensure that the data 130 and 140 is in a format acceptable for display by the patient monitor 106. The engine 160 may perform this conversion upon receiving the data. For instance, the integration engine 160 may include a plurality of well defined application programming interfaces ("APIs") configured to accept data from the respective devices 102 and 104. The APIs may define how fields or packet structure is to be converted and/or parsed for analysis and routed to corresponding fields or packets compatible with the monitor 106.

Hospital Environment Additional Embodiments

Figure 5:
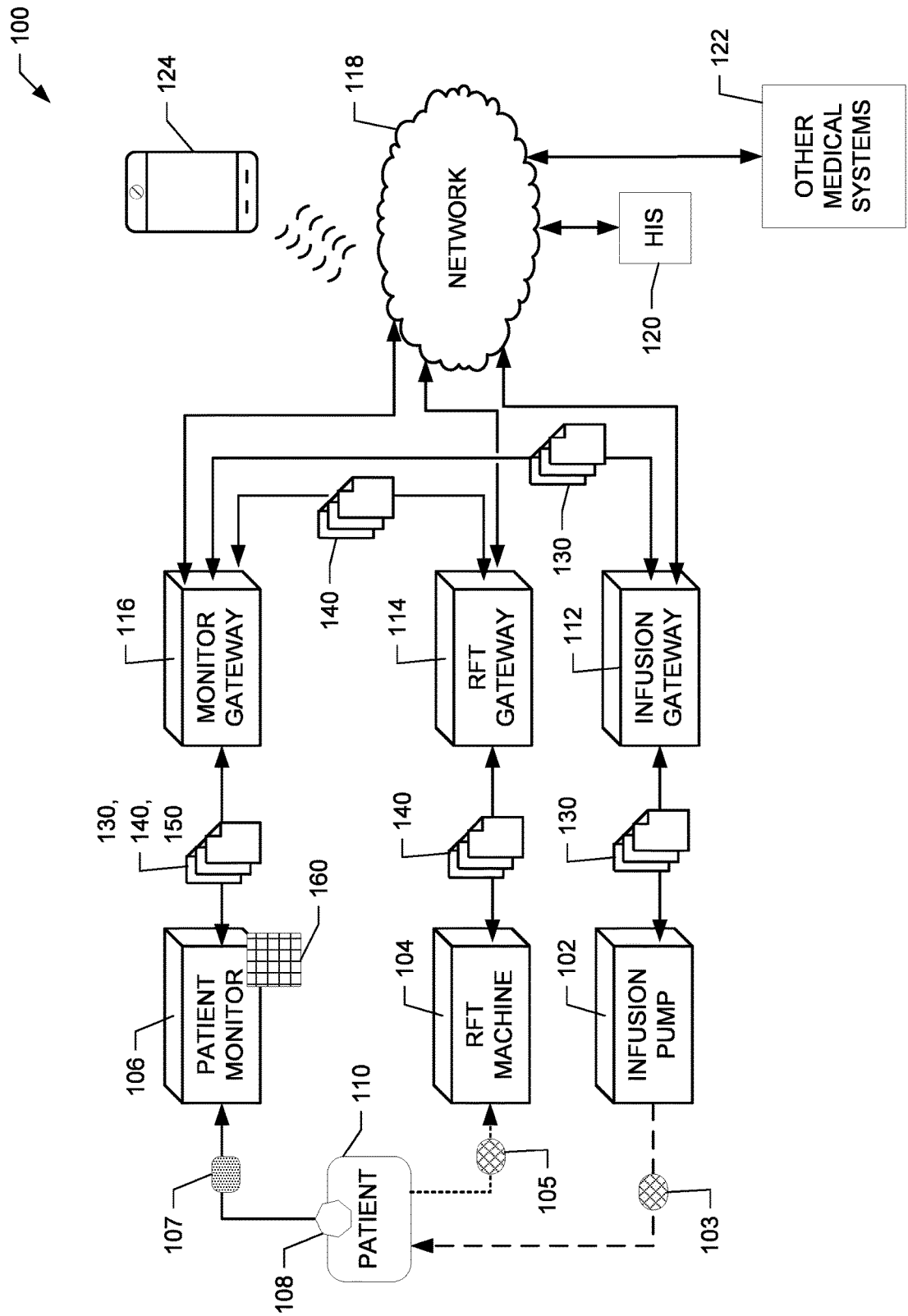
FIGS. 5 to 9 show diagrams of the hospital environment of FIG. 1 with the integration engine operating at different devices, according to example embodiments of the present disclosure.

FIGS. 5 to 9 show diagrams of the hospital environment 100 of FIG. 1 with the integration engine 160 operating at different devices, according to example embodiments of the present disclosure. For instance, FIG. 5 shows the integration engine 160 included within the patient monitor 106. In this instance, the patient monitor 106 provides the physiological data 150 to the integration engine 160 without transmission to another device. The patient monitor 106 may still send the physiological data 150 to the monitor gateway 116 for inclusion within, for example, an EMR. The use of the integration engine 160 at the patient monitor 106 may provide relatively faster responses to a user's input and/or may make customization of routines at the patient bedside easier. For instance, a clinician may use the user interface 402 of the patient monitor to select which data is to be displayed instead of having to connect or access the monitor gateway 116 to make the selection.

Figure 6:
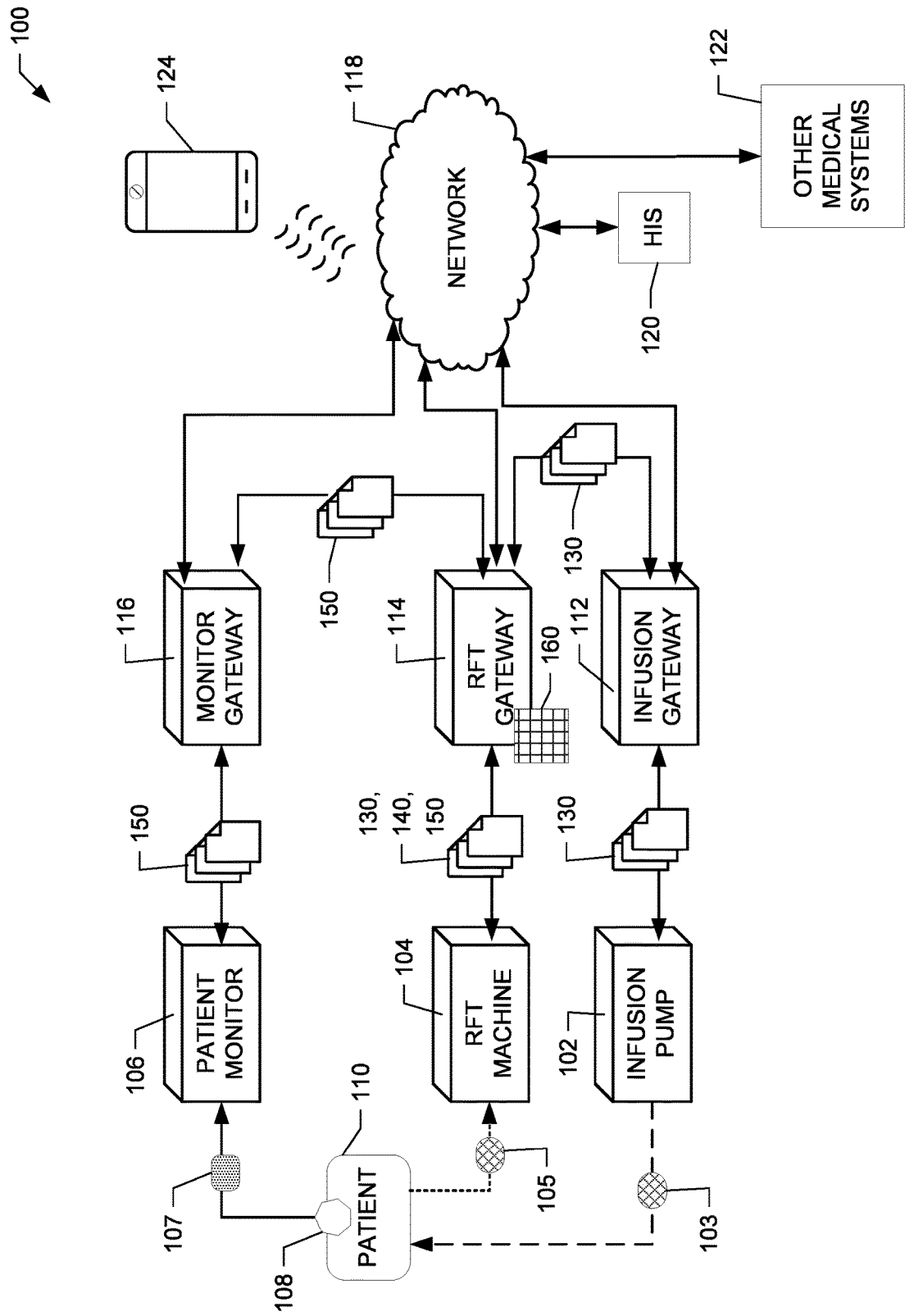
Figure 7:
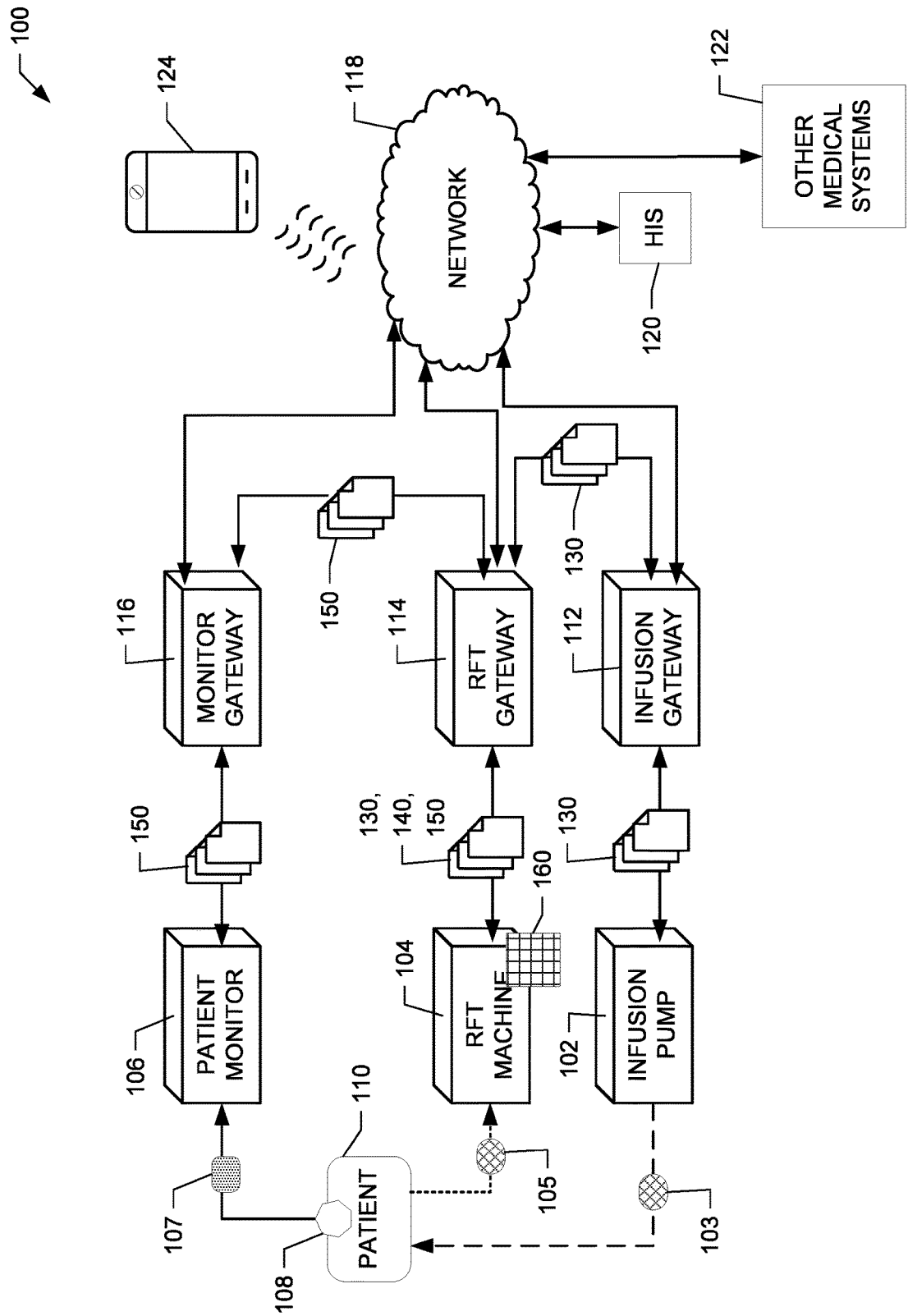

FIGS. 6 and 7 illustrate that the integration engine 160 may be included at the RFT gateway 114 and/or the RFT machine 104. In these instances, the scanning of the patient's identifier at the RFT machine 104 causes the RFT machine 104 and/or the RFT gateway 114 to broadcast to the monitor gateway 116 and the infusion gateway 112 that data including the patient identifier is to be routed to the RFT gateway 114. Alternatively, the scanning of the patient identifier at the RFT machine 104 causes the RFT machine 104 and/or the RFT gateway 114 to subscribe at the infusion gateway 112 to the data 130 related to the patient identifier and subscribe at the monitor gateway 116 to the data 150 related to the patient identifier. The subscription to the data causes the infusion gateway 112 and the monitor gateway 116 to transmit the data 130 and 150 that includes the patient identifier to the RFT gateway 114 for display at the RFT machine 104. In this instance, the integration engine 160 is configured to convert the data 130 and 150 into a format that is compatible with the RFT machine 104. Such a configuration may be desired when, for example, only a RFT machine and an infusion pump are connected to the patient 110. It should also be appreciated that such a configuration eliminates the need for the patient monitor 106 if the sensors 108 may be communicatively coupled to the RFT machine 104 and/or the infusion pump 102.

Figure 8:
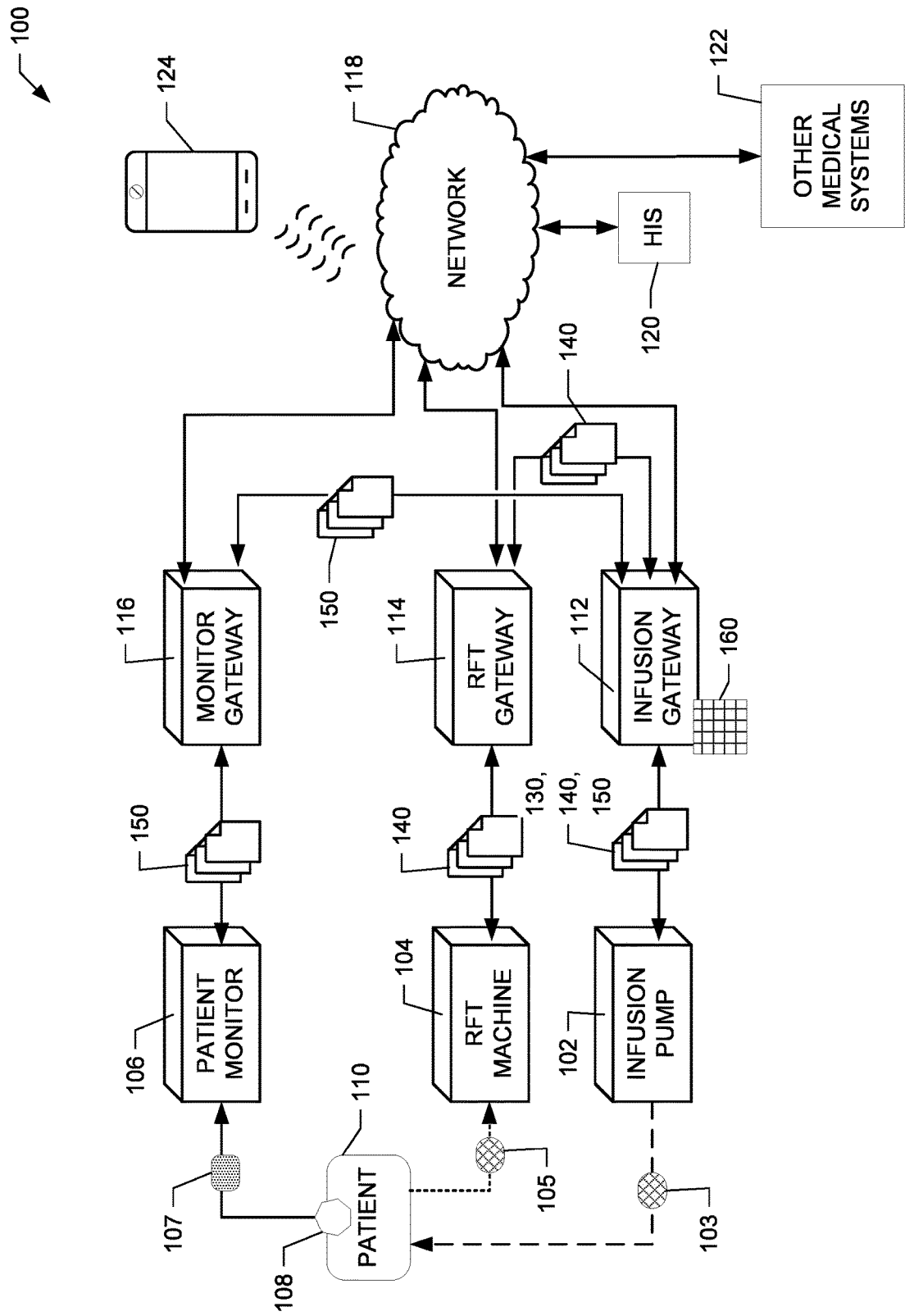
Figure 9:
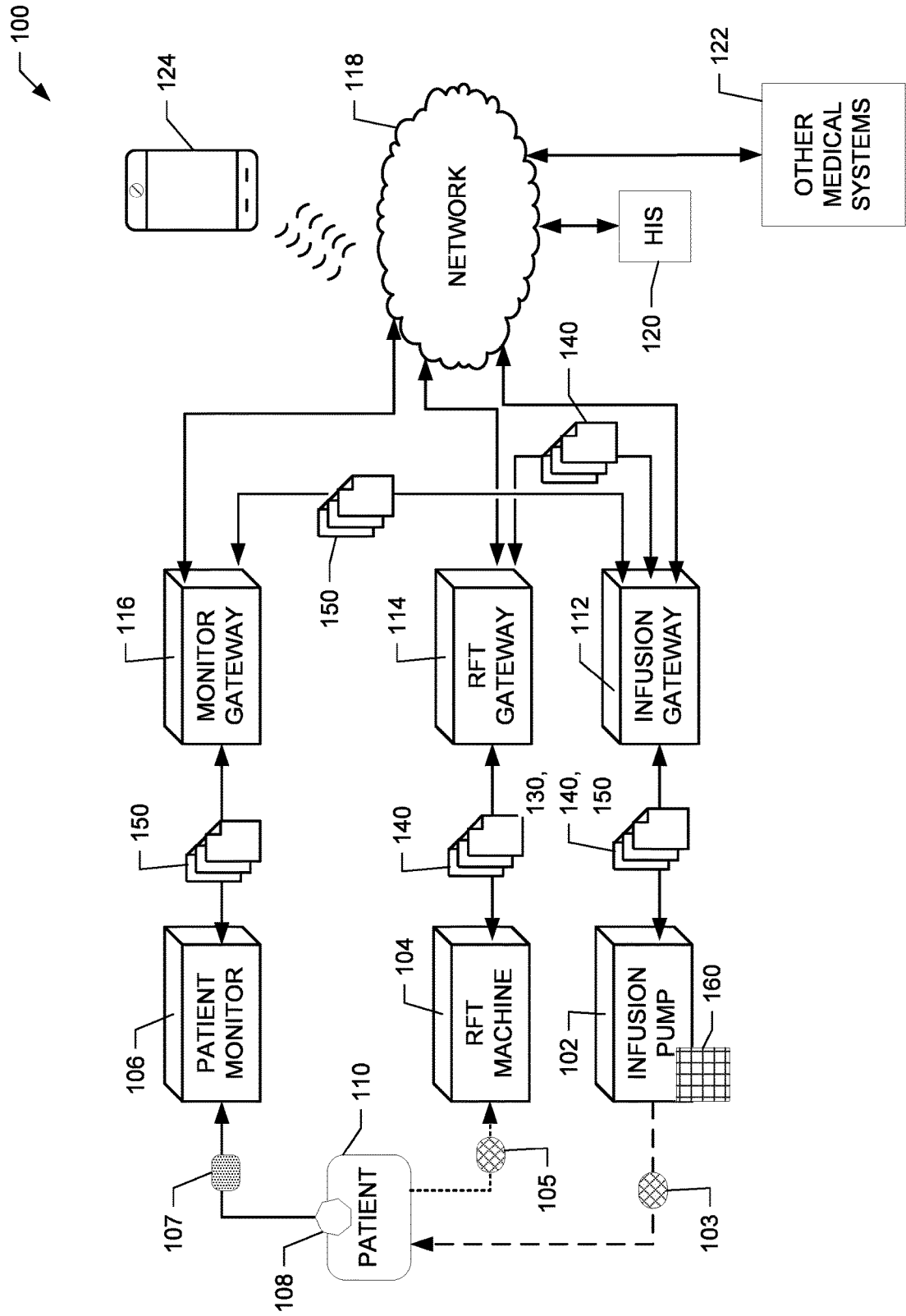

FIGS. 8 and 9 illustrate that the integration engine 160 may be included at the infusion gateway 112 and/or the infusion pump 102. In these instances, the scanning of the patient's identifier at the infusion pump 102 causes the infusion pump 102 and/or the infusion gateway 112 to broadcast to the monitor gateway 116 and the RFT gateway 114 that data including the patient identifier is to be routed to the infusion gateway 112. Alternatively, the scanning of the patient identifier at the infusion pump 102 causes the infusion pump 102 and/or the infusion gateway 112 to subscribe at the RFT gateway 114 to the data 140 related to the patient identifier and subscribe at the monitor gateway 116 to the data 150 related to the patient identifier. The subscription to the data causes the RFT gateway 114 and the monitor gateway 116 to transmit the data 140 and 150 that includes the patient identifier to the infusion gateway 112 for display at the infusion pump 102. The integration engine 160 is configured to convert the data 140 and 150 into a format that is compatible with the infusion pump 102. Again, such a configuration may be desired when, for example, only a RFT machine and an infusion pump are connected to the patient 110. This configuration may eliminate the need for the patient monitor 106 if the sensors 108 may be communicatively coupled to the RFT machine 104 and/or the infusion pump 102.

Integration Engine Embodiment

Figure 10:
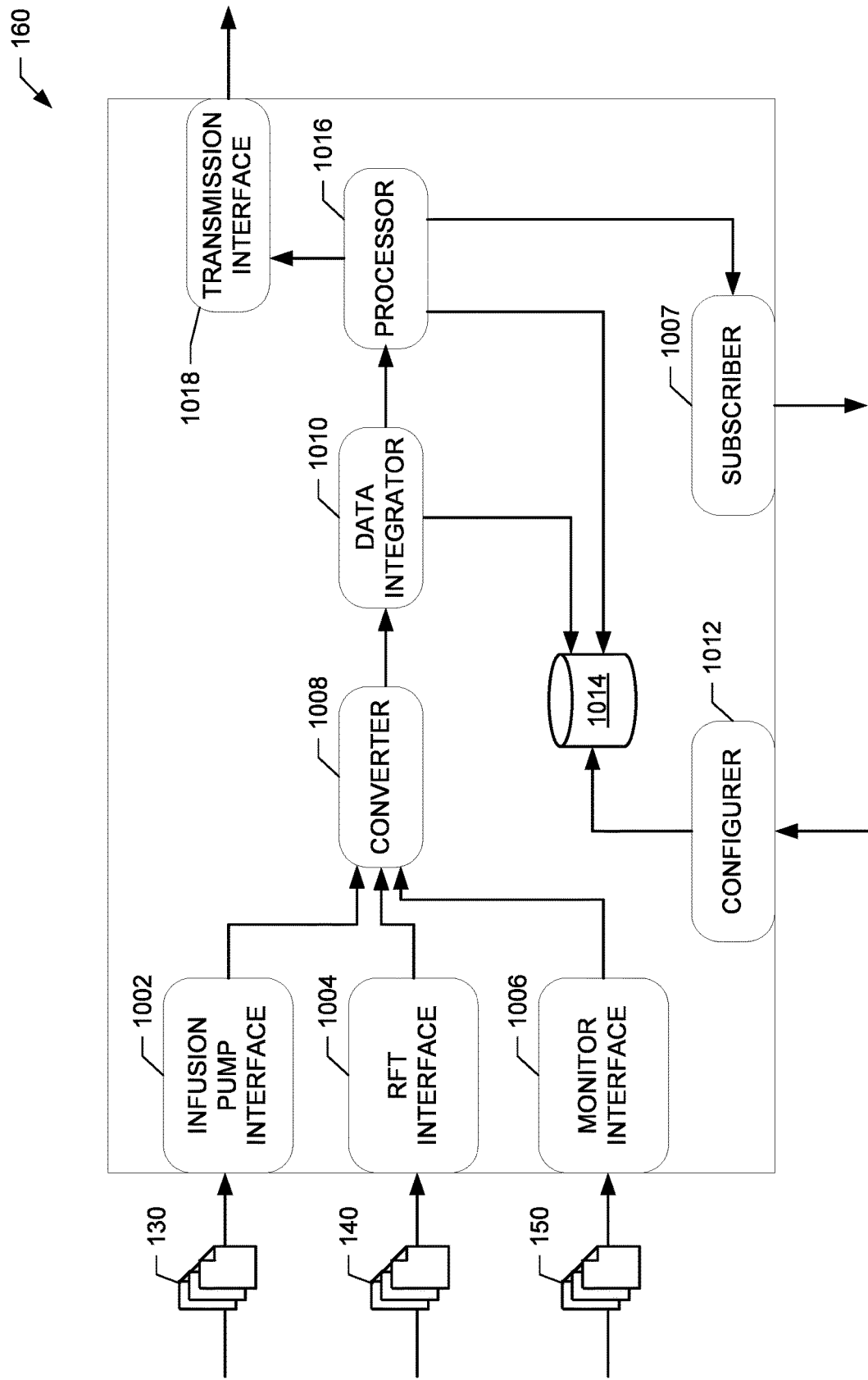
FIG. 10 shows a diagram of the example integration engine of FIGS. 1 and 5 to 9, according to example embodiments of the present disclosure.

FIG. 10 shows a diagram of the example integration engine 160 of FIGS. 1 and 5 to 9, according to example embodiments of the present disclosure. As discussed above, the integration engine 160 may be included within any one of the medical devices 102, 104, and 106 and/or any one of the gateways 112, 114, and 116. Further, the integration engine 160 may be distributed across more than one device and/or implemented on other devices, such as a server. It should be appreciated that the integration engine 160 described in conjunction with FIG. 10 is only one embodiment and that other embodiments may include fewer or additional components.

The components shown in FIG. 10 may be implemented as separate application specific integrated circuits, implemented within one or more application specific integration circuits, and/or defined as computer-readable instructions, which when executed cause circuitry and/or a processor to perform one or more specially configured operations related to the reception, aggregation, integration, conversion, and/or processing of the data 130, 140, and 150 (and derivatives thereof) for display in a single user interface.

The example integration engine 160 includes an infusion pump interface 1002 to receive the infusion therapy progress data 130, a dialysis interface 1004 to receive the renal failure therapy progress data 140, and a monitor interface 1006 to receive the physiological data 150. The interfaces 1002, 1004, and 1006 may include well-defined APIs configured to receive the data according to a defined format. Alternatively, the interfaces 1002, 1004, and/or 1006 may include web interfaces to receive, for example, the data 130, 140, and 150 via packets over an HTTP protocol.

The integration engine 160 may include multiple versions of each of the interfaces 1002, 1004, and/or 1006 (e.g., different APIs) for compatibility with different data standards, protocols, formats, etc. For instance, the integration engine 160 may include a first infusion pump interface 1002 to receive infusion data associated with a first standard and a second infusion pump interface 1002 to receive infusion data associated with a second standard. The infusion gateway 112, for example, may have well-defined ports and/or interfaces associated with each standard that are communicatively coupled to the respective infusion pump interface 1002 at the integration engine 160. Such a configuration automatically routes infusion therapy progress data 130 of each standard to the appropriate infusion pump interface 1002. It should be appreciated that the gateways 114 and 116 may be similarly configured as the infusion gateway 112.

Additionally or alternatively, the integration engine 160 may include a router configured to route the infusion therapy progress data 130 to the appropriate version of the infusion pump interface 1002. For instance, a router may compare data packet headers, identifiers, or other indicia (e.g., data types, labels, etc.) indicative of the standard to one or more routing tables. A routing table specifies to which of the interfaces 1002 the data 130 is to be routed based on determined standard. Responsive to determining the standard, the router transmits the data to the appropriate infusion pump interface 1002 for conversion into a common format. It should be appreciated that routers may also exist for the interfaces 1004 and 1006.

The data 130, 140, and 150 received at the interfaces 1002, 1004, and/or 1006 may be streamed or transmitted periodically from the respective gateways 112, 114, and 116 and/or the medical devices 102, 104, and 106. In some instances, the interfaces 1002, 1004, and 1006 may be configured to request the data 130, 140, and 150 from the respective gateways 112, 114, and 116 and/or the medical devices 102, 104, and 106. In these instances, the request may include the patient identifier and/or an indication of which types of data are to be received.

To receive the data 130, 140, and 150, the example integration engine 160 includes a subscriber 1007. The example subscriber 1007 is configured to receive an indication as to which patient is located adjacent to which medical devices. For instance, if the integration engine 160 is located at the monitor gateway 116, the patient monitor 106 may provide a patient identifier as well as a MAC address or IP address. The IP or MAC address is used by the integration engine 160 as a destination address for packets or data that is transmitted for display. The subscriber 1007 is configured to transmit the patient identifier to the gateways 112 and 114 (in instances where the engine 160 is at the gateway 116) to subscribe to the data 130 and 140 that includes the patient identifier. Subscribing causes the gateways 112 and 114 to transmit any of the data 130 and 140 with the specified criteria to the integration engine 160.

Alternatively, the gateway 116 (and the integration engine 160) may receive all the data from the gateways 112 and 114. In this instance, the subscriber 1007 operates with the interfaces 1002, 1004, 1006, converter 1008, and/or data integrator 1010 to select which of the data is to be processed and/or displayed. In some of these instances, the subscriber 1007 may provide the patient identifier to the monitor gateway 116, which filters by patient identifier and transmits the filtered data to the interfaces 1002, 1004, and 1006.

The subscriber 1007 may also subscribe to certain data types in addition to data related to a patient. For example, configuration or setup at the monitor 106 may include specifying that all infusion rate data is to be displayed. The integration engine 160 receives this configuration information via configurer 1012, which is transmitted to the subscriber 1007. The example subscriber 1007 determines one or more parameters, data labels, and/or corresponding data identifiers associated with infusion rate and transmits one or more subscription messages to the infusion gateway 112, including the patient identifier and identifiers of the desired parameter (e.g., infusion rate, drug name, pump identifier, etc.). This causes the infusion gateway 112 to only send the relevant data that includes the specified parameters or identifiers, thereby reducing the amount of data transmitted through the hospital environment 100 and processed by the integration engine 160.

The example subscriber 1007 is dynamic. For instance, during a treatment, a clinician at the monitor 106 may specify to also view infusion dose. This causes a message to be sent from the monitor 106 to the integration engine 160 (via configurer 1012), which determines (via the subscriber 1007) one or more infusion parameters (and corresponding identifier(s)) associated with infusion dose data. The subscriber 1007 then sends a subscription message to the infusion gateway 112 with the identifiers of the desired dose data.

The example integration engine 160 of FIG. 10 also includes a converter 1008 configured to format or otherwise convert the received data 130, 140, and 150 into a form that is compatible with the device that is to display the data (e.g., the patient monitor 106). The converter 1008 may include separate modules or interfaces for receiving data of different standards from respective versions of the interfaces 1002, 1004, and 1006. Conversion at each module may be conducted according to a specified routine for converting data from one standard into a normalized or common standard. For example, a module for a first standard may have definitions that relate labels of the first standard to labels for a common standard. The module uses this one-to-one or many-to-one mapping to determine how the data is to be converted.

Alternatively, the integration engine 160 may include one of each type of interface 1002, 1004, 1006. In these alternative embodiments, the converter 1008 is configured to determine a standard for the received data 130, 140, and 150. The converter 1008 then routes the received data for each standard to the appropriate data conversion algorithm or engine. For instance, the converter 1008 may include one or more well defined conversion algorithms that specify how data of certain formats or standards, or located in certain portions of a packet are to be parsed and reformatted for analysis. For example, the algorithms may include a look-up table of parameter names, labels, and/or data types related to different known medical devices to enable the converter 1008 to determine the contents of the data. It should be appreciated that the look-up table (or algorithms) may provide a conversion for each standard of supported data. Further, the look-up table (or algorithms) may be updated periodically as additional standards are created or different types of medical devices are added to the environment 100.

The example data integrator 1010 of FIG. 10 is configured to analyze the data from the different interfaces 1002, 1004, and 1006 (and derivative data thereof) and determine which data is to be displayed concurrently. The data integrator 1010 may access a database 1014 (e.g., a memory) that provides criteria as to which data is to be displayed. This is especially true in instances where the integration engine 160 receives all the data 130, 140, and 150 for a particular patient. In instances where only, certain data is subscribed to, the example data integrator 1010 still has to determine which data is from the same time period.

In an example embodiment, the data integrator 1010 may receive an instruction that data for a particular patient is to be processed for display. The data integrator 1010 accesses the database 1014 for a list of data types, parameters, or data identifiers that are to be displayed. The data integrator 1010 then parses or otherwise filters data for the particular patient that includes the specified identifiers. The data integrator 1010 also reads timestamps associated with the data to ensure data from the same time period or time frame is later processed downstream at the same time for concurrent display. In some instances, the data integrator 1010 may aggregate selected data for the same time period into one or more packets having the same timestamp.

The example configurer 1012 of FIG. 10 is configured to define lists regarding which data is to be displayed at, for example, the monitor 106. The example configurer 1012 may provide an interface or operate through the user interface 402 of the patient monitor 106. The configurer 1012 may include a list of available parameters or data types that may be displayed. The list may also include identifiers of all medical devices and sensors related to the patient. The configurer 1012 may dynamically update the list as additional devices are connected to or otherwise associated with the patient 110.

In one embodiment, a clinician may configure the monitor 106 before a treatment begins. In this instance, the configurer 1012 may provide a default list of parameters for the clinician to select. The configurer 1012 may then determine the specific device parameters or device itself as the device comes online and begins transmitting data. In this instance, the configurer 1012 enables the clinician to select which waveforms are to be displayed and then operates with the subscriber 1007 and the data integrator 1010 to ensure that the desired data is displayed. If for example, data is not available, the integration engine 160 may provide an error message or a null waveform (e.g., a clinician selects to view an ultrafiltration rate of a RFT when in fact no RFT or dialysis machine is connected to the patient 110).

In another embodiment, the configurer 1012 may track which devices are associated with a patient identifier. The configurer 1012 may determine parameters or data types of each device and construct a corresponding list for the clinician to configure the monitor 106. For instance, each medical device may transmit a device identifier in conjunction with the patient identifier upon being associated with the patient. The configurer 1012 receives the message and uses the device identifiers to track which devices are connected to or otherwise related to the patient 110.

The configurer 1012 also enables a clinician or an administrator to create one or more routines or algorithms for processing and/or creating derivatives of the data 130, 140, and 150. For instance, an administrator or a clinician may use the configurer 1012 to define a calculation for total fluid input based on which devices are connected to the patient. The configurer 1012 may provide a graphical programmable interface that, for example, shows a map or illustration of the devices associated with a patient and the corresponding parameters. The clinician may drag or otherwise select the parameters associated with fluid input from the different machines into an equation, which creates a routine stored to the database 1014. A processor 1016 accesses the routine at the database 1014 to determine which and how the parameters are to be summed.

In other instances, the database 1014 may store default calculations or routines to determine commonly used derivatives of the data 130, 140, and 150. For example, a default calculation for fluid balance may specify that infusion rate data 130 is needed in addition to fluid fill and output data 140 and urine data 150. Selection of the fluid balance calculation may cause the configurer 1012 to determine that the infusion rate data 130 is needed in addition to fluid fill and output data 140 and urine data 150 for display and ensure that the appropriate devices are programmed and connected to the patient 110. During patient treatment, the processor 1016 determines the values for fluid balance based on the calculation using the infusion rate data 130 in addition to fluid fill and output data 140 and urine data 150, and provides these calculated derivative values for display.

Alternatively, an administrator may define default routines before any patient treatments. The configurer 1012 may populate the routines based on which devices are connected to the patient and/or preferences of a clinician. For example, an administrator may create via the configurer 1012 a default definition of fluid intake, which may specify that an infusion rate from all infusion pumps connected to a patient are summed with dialysis fluid provided into a patient's peritoneal cavity in addition to any information received from a nutritional feeding system. The configurer 1012 may receive a message from the monitor that a clinician desires to view the fluid intake parameter, which causes the configurer 1012 to determine (if already not completed) which infusion pumps, RFT machines, and nutritional feeding systems are connected to the patient. The configurer 1012 then searches for the infusion rate, dialysis rate, and feeding rate parameters from those machines and populates the routine accordingly.

The example processor 1016 of FIG. 1 is configured to determine any parameters or derivatives of the data 130, 140, and 150 based on one or more routines and/or algorithms stored within the database 1014. The example processor 1016 for example, uses one or more routines to determine total fluid input to a patient, total fluid output from a patient, and net total fluid within the patient. The processor 1016 performs the one or more routines for every instance or timestamp of the converted and integrated data 130, 140, and 150.

The example processor 1016 may also operate with the configurer 1012 to provide user interface functionality with the data. For instance, the processor 1016 may define one or more actions that may be performed contingent upon a user selecting a portion of a waveform displayed at the monitor 106. Specifically, the processor 1016 may create a menu option box that is hidden from display until a user selects a waveform. Selection of a menu option may change which data is to be displayed. The example processor 1016 and/or the configurer 1012 updates a list within the database 1014 with the new selection by the user, which causes the data integrator 1010 to possibly select additional or less data for processing and causes the processor 1016 to perform more or fewer routines.

The processor 1016 may also operate one or more routines related to alarms, alerts or events. For instance, the processor 1016 may compare specified data to limits or trends of data to limits to determine if an alert or event is to be generated. The processor 1016 may transmit a message to the monitor 106 causing the alarm or event to be displayed. It should be appreciated that the routines may be complex with the ability to take into account data from a wide variety of medical devices. For example, certain alarm limits may be adjusted based on whether an infusion or dialysis is occurring. In another instance, an alarm for a limit on the amount of fluid placed into a patient may be delayed upon determining a RFT machine is about to begin a drain phase.

The example processor 1016 also formats the data for display, including transmitting data associated with the same timestamp at the same time (or as close as possible) to the monitor 106. The processor 1016 may further format the data to be compatible with the patient monitor 106. For instance, the processor 1016 may provide indications regarding which data is to be displayed at certain screen locations on the monitor 106. The clinician may provide the initial determination, which is included by the processor 1016 in one or more messages to the monitor 106. Alternatively, the processor 1016 may determine the order based on predetermined importance of the different parameters or data types.

The example transmission interface 1018 of the integration engine 160 is configured to transmit data for display within the user interface 402 of the patient monitor 106, for example. The transmission may include data packets. Alternatively, the transmission may include a stream of data. In some instance, the transmission interface 1018 may transmit the data periodically, such as every 5 or 10 seconds. Alternatively, the transmission interface 1018 may queue the data until a request message is received from the patient monitor 106.

Based on the above disclosure, it should be appreciated that the integration engine 160 improves the performance of the hospital environment 100 by simultaneously processing thousands of pieces of data (in different formats) from hundreds or thousands of medical devices such that only specified data for a particular patient is displayed on a single user interface. The integration engine 160 also includes logic, algorithms, or routines to determine parameters, events, or alarms from the received data and make these parameters, events, and alarms also for display within the user interface. Such an operation is beyond the capabilities of a general purpose computer operating general or generic functions.

Flowchart of Example Integration Engine Data Processing Embodiment

Figure 11:
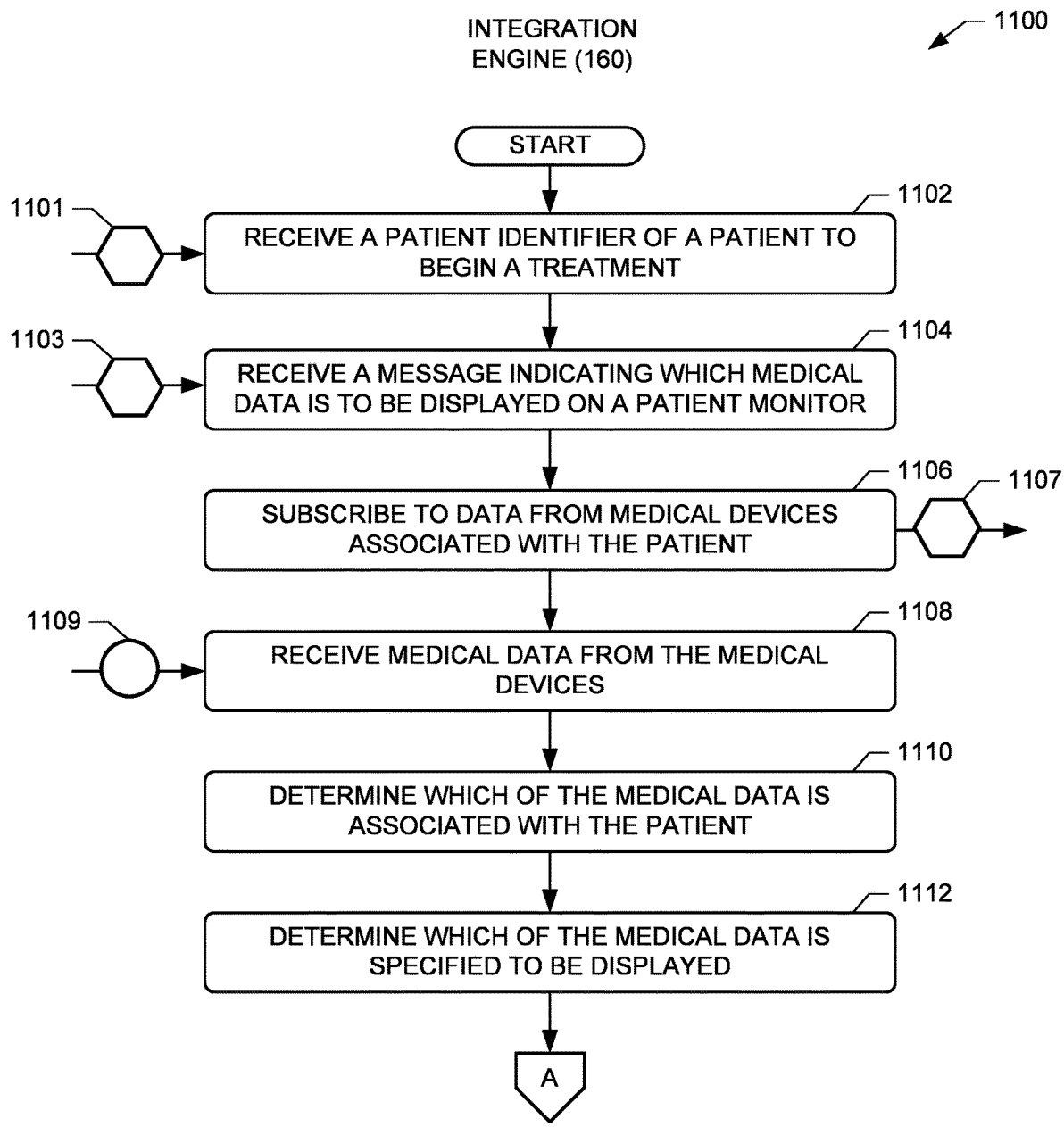
FIGS. 11 and 12 show a flow diagram illustrating an example procedure to display medical data from multiple medical devices on a single display, according to an example embodiment of the present disclosure.
Figure 12:
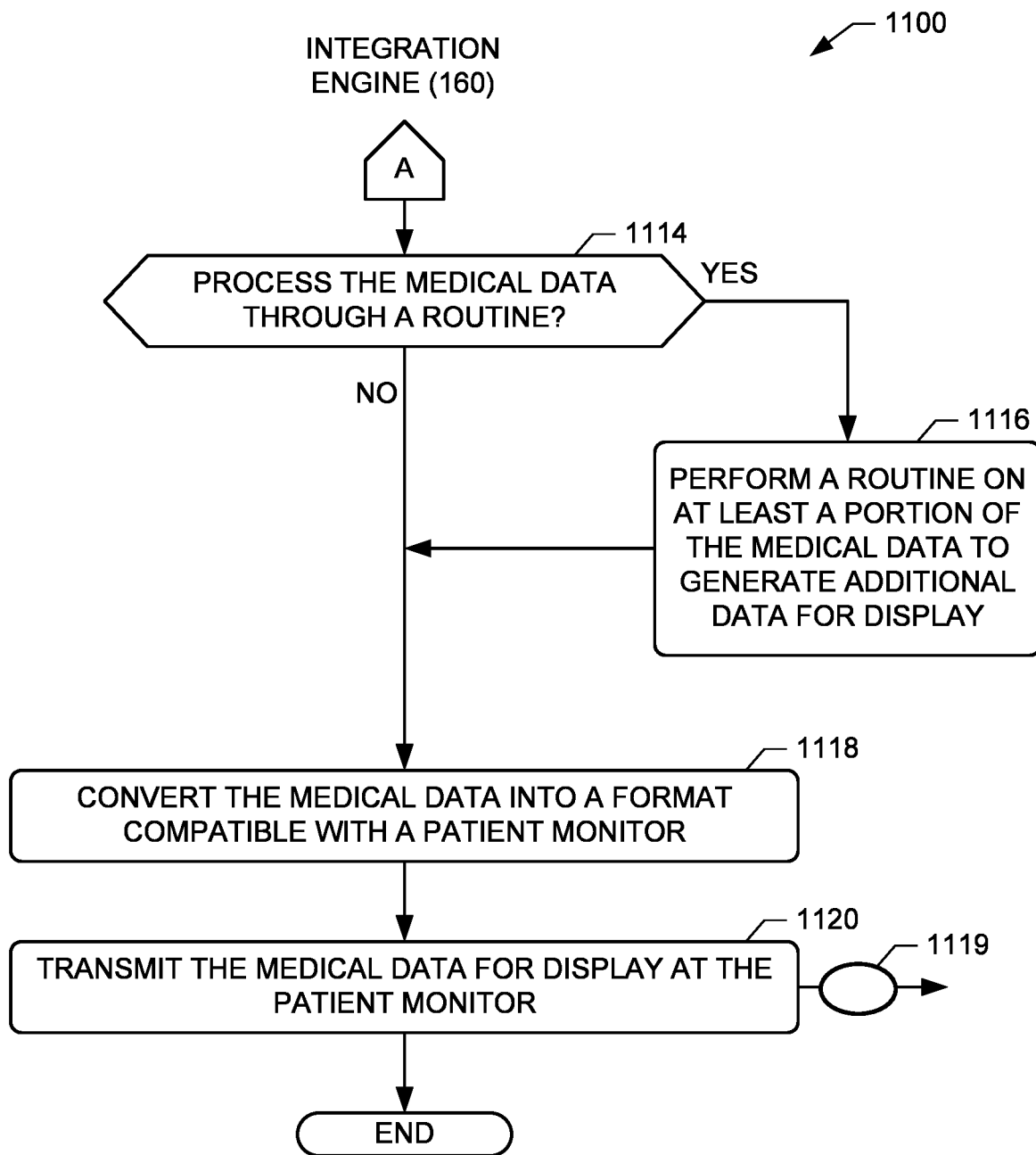

FIGS. 11 and 12 show a flow diagram illustrating an example procedure 1100 to process medical data from different medical devices for display at a user interface, according to an example embodiment of the present disclosure. The example procedure 1100 may be carried out by, for example, the integration engine 160 described in conjunction with FIGS. 1 to 10. Although the procedure 1100 is described with reference to the flow diagram illustrated in FIGS. 11 and 12, it should be appreciated that many other methods of performing the functions associated with the procedure 1100 may be used. For example, the order of many of the blocks may be changed, certain blocks may be combined with other blocks, and many of the blocks described are optional.

Procedure 1100 begins when the integration engine 160 receives a message 1101 that includes a patient identifier of a patient that is to undergo a treatment (block 1102). The integration engine 160 may also receive an indication as to which medical devices are associated with the patient identifier. In some instances, the integration engine 160 may query some or all of the gateways 112, 114, and/or 116 to determine which medical devices are associated with the patient. In these examples, the medical devices may prompt a clinician to enter a patient identifier or scan a barcode associated with the patient prior to programming or beginning treatment. In these examples, the patient identifier may be included within a header of the medical data. Additionally or alternatively, the integration engine 160 may query the HIS 120 for the patient-device association. In these examples, the downstream HIS 120 may make the association or determine the association between medical devices and patients.

The integration engine 160, executing procedure 1100, may also receive one or more messages 1103 indicative of which medical data is to be displayed at a patient monitor (block 1104). The messages 1103 may specify a name or identifier of a medical device parameter corresponding to a waveform or numerical value. In some instances, the integration engine 160 may determine the identifiers as specified by the generating medical device based on the parameters or parameter names input at the patient monitor.

Figure 13:
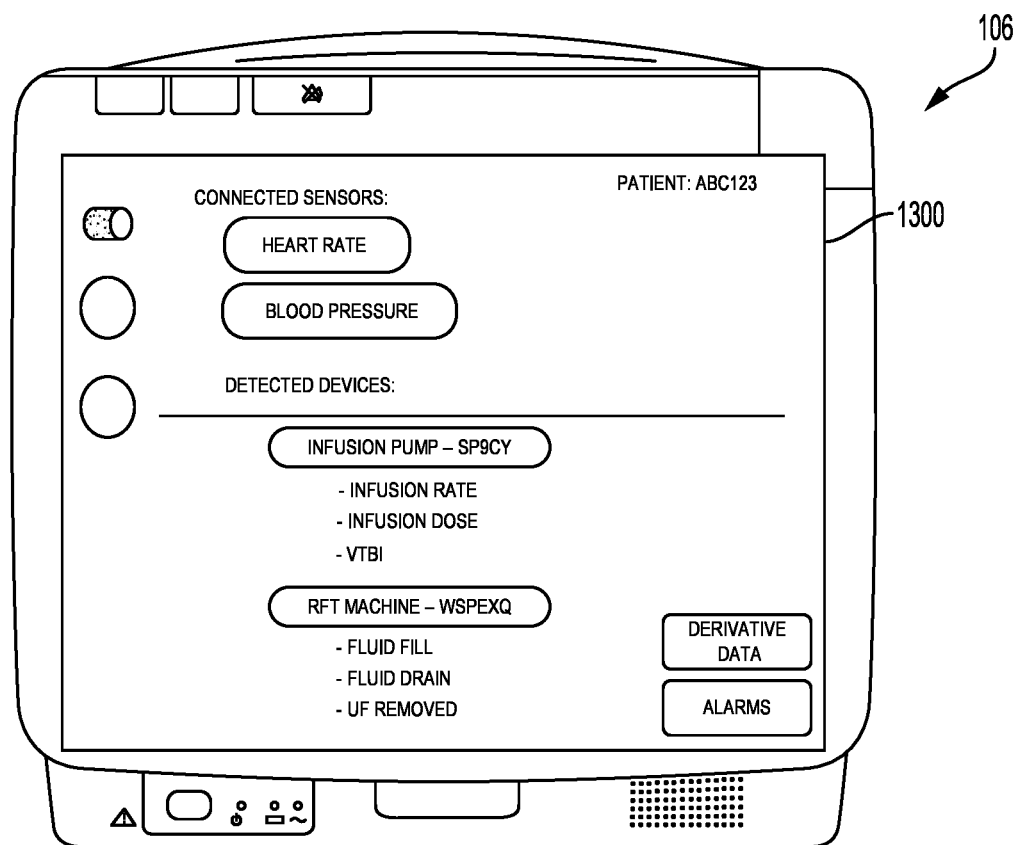
FIGS. 13 and 14 show diagrams of the patient monitor of FIG. 4, providing configuration parameters for displaying data from the example integration engine of FIGS. 1 and 5 to 9, according to example embodiments of the present disclosure.

FIG. 13 shows a diagram of an example configuration user interface 1300 that may be operated by the integration engine 160 and displayed by the patient monitor 106, according to an example embodiment of the present disclosure. In this example, the integration engine 160 determines which medical devices are associated with ABC123 patient. This includes detecting which medical devices are directly or indirectly connected to the monitor 106, which may include a heart rate sensor and/or a blood pressure sensor. Accordingly, the integration engine 160 causes the patient monitor 106 to display icons indicative of the connected sensors. A user may select any or each of the sensors, causing the integration engine 160 to determine information about the sensors (e.g., identifier, data type(s), data standard, etc.) and whether the sensor is configurable. For example, the integration engine 160, through the user interface 1300, may enable a user to select which types of data is output by a sensor and/or how often the data is transmitted.

The example user interface 1300 also displays medical devices that are not connected to the monitor 106 but which are determined to be associated with the patient. In the illustrated example, the associated patient devices include the SP9CY infusion pump 102 and the WSPEXQ peritoneal RFT machine 104. The integration engine 160, through polling of the devices (or through libraries defining configurations), determines which parameters of medial data are outputted (or selected to be output based on therapy type of clinician selection) by each device. For instance, the infusion pump is to transmit infusion rate therapy progress data 130, infusion dose therapy progress data 130, and volume to be infused ("VTBI") therapy progress data 130. The integration engine 160, through the user interface 1300, enables a clinician to select which of the data is to be displayed on the monitor 106 during treatment. In some examples, a clinician may select each of the parameters, causing the integration engine 160 to query the medical device for (or otherwise determine) operation information. The integration engine 160, through the user interface 1300, then enables a user to change therapy parameters or settings, which causes the integration engine 160 to send one or more messages to the appropriate medical device with the programming instructions. In this manner, the integration engine 160 enables a clinician to program the medical devices connected to or otherwise associated with a patient from one device, for example, the monitor 106.

Figure 14:
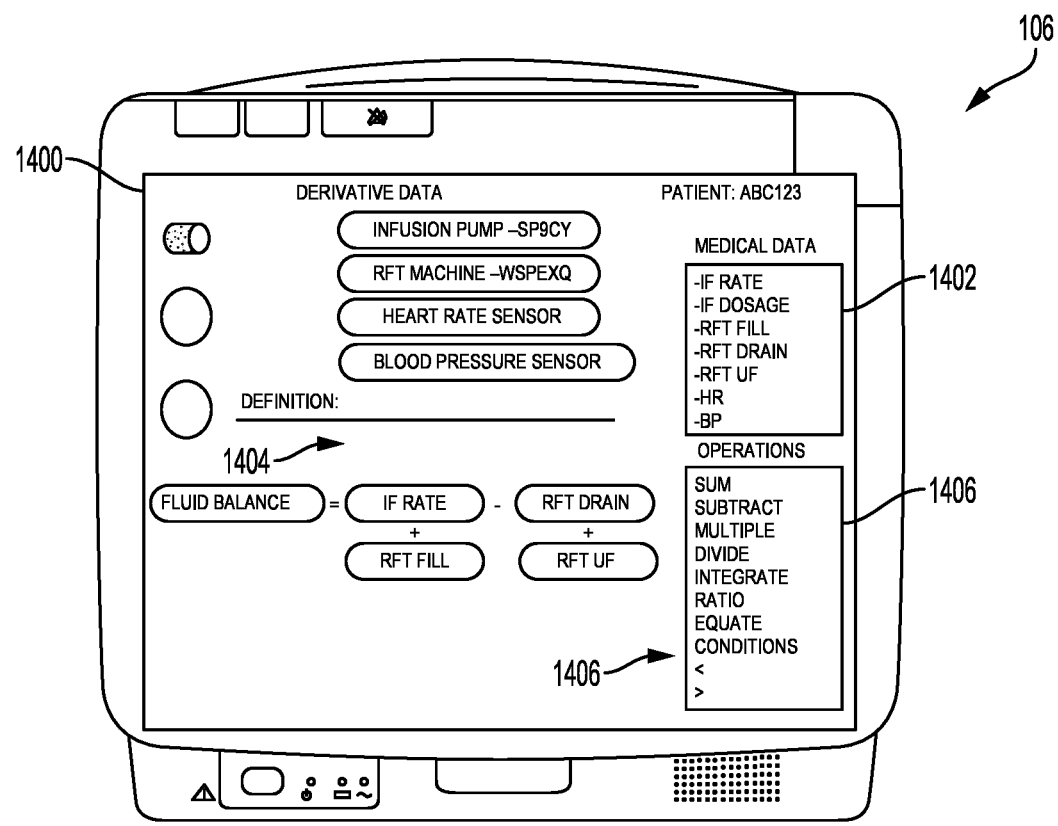

The example user interface 1300 also includes features that enable a clinician to program or configure alarms and/or derivative data. FIG. 14 shows a diagram of an example derivative data configuration user interface 1400 that may be operated by the integration engine 160 and displayed by the patient monitor 106, according to an example embodiment of the present disclosure. Selection of the 'Derivative Data' icon on the user interface 1300 may cause the integration engine 160 to display the user interface 1400. The integration engine 160, through user interface 1400, enables a clinician to select derivate data to display on the monitor 106 and/or to create a new type of derivate data based on medical device. The user interface 1400 includes a list of medical devices related to Patient ABC123, which includes an infusion pump, RFT machine, heart rate sensor, and blood pressure sensor. The user interface 1400 also includes a section 1402 that displays which medical data is available from the medial devices.

The example user interface 1400 also displays a definition section 1404 that is configured to specify how derivate data is derived. In some instances, the definition may be pre-defined or pre-specified. For example, the user interface 1400 may include a section (not shown) of available types of derivative data based on the available types of medical data. To determine the types of available derivate data, the integration engine 160 may compare the available types of medical data in section 1402 to a list of derivative data that identifies all of the variables of medial data needed to be available to enable the derivative data to be determined. In some instances, a clinician may select certain derivative data, and the integration engine 160 may provide an indication as to which medical data is still needed. Such an indication may be provided as an instruction or reminder to the clinician about additional devices that need to be connected to or associated with the patient.

In the illustrated example of FIG. 14, the user interface 1400 within section 1404 is configured to enable a clinician to graphically create derivative data. For example, the user interface 1400, via the integration engine 160, enables a clinician to select and drag medial data to section 1404, which creates a graphical representation. The user interface 1400 also enables the clinician to select operations from section 1406 to specify a relationship between the data. Such a configuration specially programs the integration engine 160 to determine the derivative data using the routine specified graphically by the clinician. In this example, a clinician specifies how fluid balance derivate data is determined from a combination of infusion therapy data 130 and RFT data 140. It should be appreciated that the integration engine 160 may provide a similar interface to facilitate the specification of conditions/thresholds for alarms and/or alerts.

Returning to FIG. 11, after data selection and/or configuration, the integration engine 160 uses the patient identifier and/or the medical data to subscribe or otherwise receive or filter the identified medical data associated with the identifier patient (block 1106). For example, the integration engine 160 may transmit one or more messages 1107 to the appropriate gateway 112, 114, and/or 116 to receive the selected or requested medical data 130, 140, and/or 150. The messages 1107 may include an IP address or other address/identifier/port interface number associated with the integration engine 160. The messages 1107 may also include an identifier or data label of the requested medical data.

The integration engine 160 then receives medical data from the medical devices (block 1108). The medical data may be received within one or more messages and/or packets 1109 from, for example, the gateways 112, 114, 116, and/or the patient monitor 106. The integration engine 160 may determine which of the data is associated with the patient and/or identified parameters (block 1110). For instance, the integration engine 160 may manage medical data processing for hundreds of patients, each associated with two or more medical devices outputting at least one parameter of medical data or therapy progress data. In other words, the integration engine 160 may subscribe to a significant amount of medical data that needs to be organized by patient, medical device, parameter, timestamp, etc. It should be appreciated that this step may be omitted when the integration engine 160 is configured to subscribe or receive medical data related to only one patient.

The integration engine 160 determines which of the identified data is to be displayed based on the previously received message(s) 1103 at block 1104 (block 1112). The integration engine 160 determines if one or more routines or algorithms are to be operated to further process the medical data to determine derivative data (block 1114). For instance, if the integration engine 160 determines that total fluid input, total fluid output, and net fluid parameters are to be determined and displayed at the monitor, the integration engine 160 operates the associated routines for determining these parameters (block 1116). The integration engine 160 may then convert the medical data for display into a format that is compatible with the patient monitor (block 1118). In some examples, this step may instead be performed after the medical data from the medical devices is received. The integration engine 160 then transmits the medical data to the patient monitor for display (block 1120). It should be appreciated that blocks 1108 and 1120 may be continuously looped through as long as the patient is undergoing the treatment and/or until all of the medical devices have been deactivated or dissociated from the patient. At this point, the example procedure 1100 ends with respect the patient being monitored.

Data Conversion Embodiment

Figure 15:
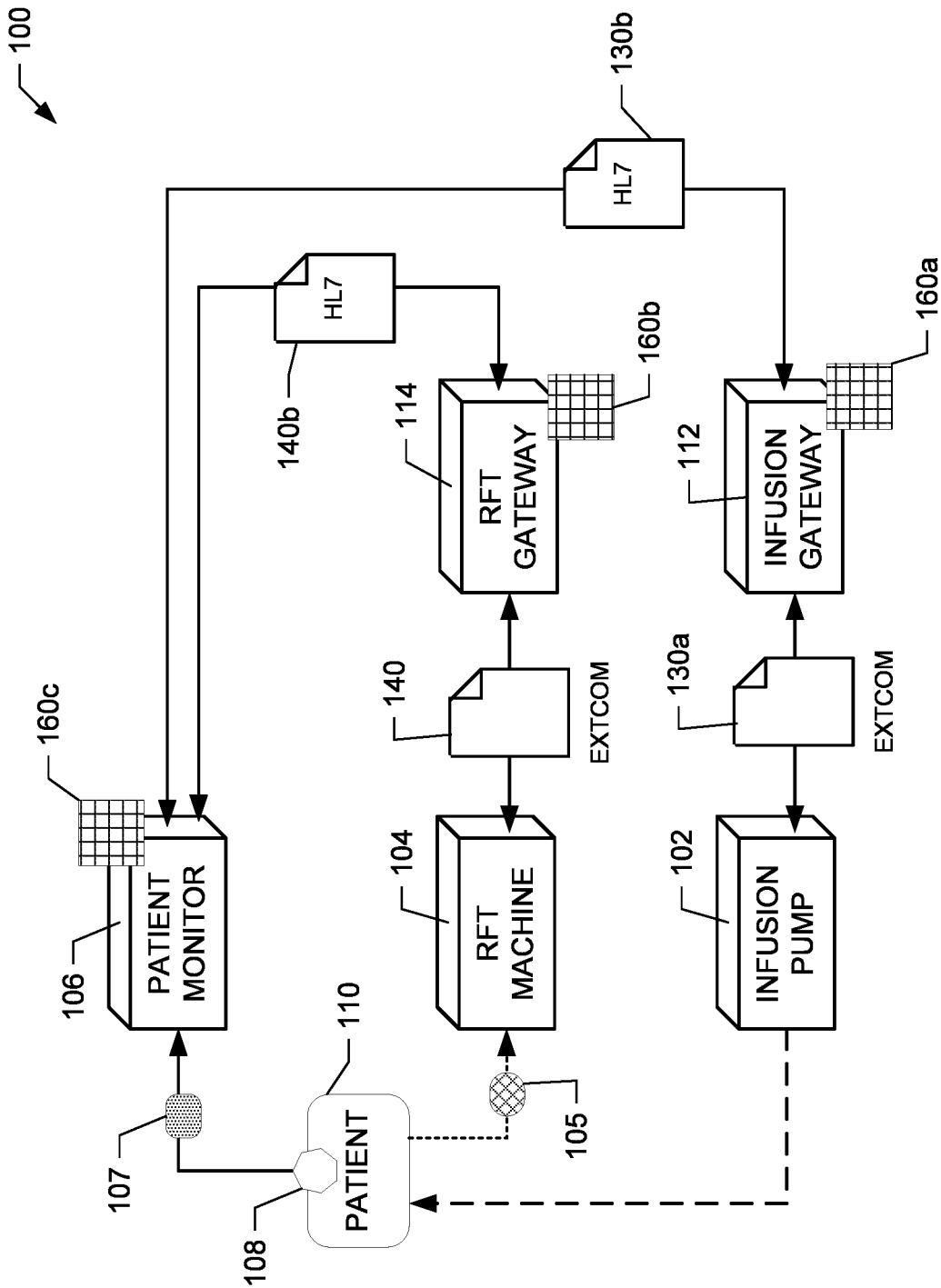
FIG. 15 shows a diagram of data conversion provided by one or more integration engines within the example hospital environment of FIG. 1, according to example embodiments of the present disclosure.

As discussed above, the example integration engine 160 of FIGS. 1 and 5 to 12 is configured to convert or otherwise convert medical data 130 and 140 from one standard, format, language, or protocol into another standard, format, language, or protocol that is compatible with the HIS 120 or another medical device. FIG. 15 shows a diagram of data conversion provided by one or more integration engines 160 within the example hospital environment 100 of FIG. 1, according to example embodiments of the present disclosure. In the illustrated example, the infusion gateway 112 includes a first integration engine 160*a*, the RFT gateway 114 includes a second integration engine 160*b*, and the patient monitor 106 includes a third integration engine 160*c* (the monitor gateway 116 is omitted). However, in some alternative embodiments, the monitor gateway 116 may be included within the environment 100 and operate the integration engine 160*c*.

In the example of FIG. 15, the infusion pump 102 and the RFT machine 104 are configured to operate using the EXTCOM protocol (i.e., a Baxter® proprietary communication protocol). The patient monitor 106 is configured to operate using the Health Level 7 ("HL7") protocol. In known hospital systems, the infusion pump 102 and the RFT machine 104 would not be capable of communicating with the patient monitor 106 because of the use of different protocols.

The EXTCOM protocol uses Extensible Markup Language ("XML") encoding syntax that includes a header, body, and session token identifier. The header includes fields that specify, for example, an EXTCOM protocol version, transmitting device serial number, destination address, message timestamp, unique message identifier, a type of EXTCOM message, an encryption flag, and an authentication token. The header may also specify a device EMR identifier for configuration with, for example, the HIS 120. The message type may include a status message, a configuration message, a setup message, a drug library message, a pump query message, or an infusion order message.

The HL7 protocol also includes XML encoding syntax. Some portions of the HL7 protocol include message headers that are similar to the EXTCOM protocol, including protocol version, transmitting device serial number, destination address, message timestamp, unique message identifier. However, the HL7 protocol uses different labels for the header fields compared to the EXTCOM protocol. In addition, the HL7 protocol may include additional header fields including an interaction identifier, a processing code, device type identifier, a transmitting device location identifier, and a receiving device location identifier.

The RFT machine 104 and the infusion pump 102 are configured to receive and process EXTCOM messages. This means that the RFT machine 104 and the infusion pump 102 are programmed to search for header and body information using certain labels to identify fields. The use of different labels and message structure make it difficult, if not impossible for the RFT machine 104 and the infusion pump 102 to receive and process HL7 messages.

To overcome these limitations, the first integration engine 160a is configured to convert data transmitted to the infusion pump 102 into the EXTCOM protocol. The first integration engine 160a is also configured to convert data received from the infusion pump 102 into HL7 protocol. Similarly, the second integration engine 160b is configured to convert data transmitted to the RFT machine 104 into the EXCOM protocol. The second integration engine 160b is also converts data received from the RFT machine 104 into the HL7 protocol. The third integration engine 160c is configured to receive and display data 130 and 140 from the respective medical devices 102 and 104 in the HL7 protocol. In some examples, the integration engines 160a and 160b may be integrated with the integration engine 160c at the patient monitor 106 and/or the monitor gateway 116.

In the illustrated example shown in FIG. 15, the infusion pump 102 (during treatment of the patient 110) transmits infusion therapy progress data 130a formatted in the EXTCOM protocol to the infusion gateway 112. The first integration engine 160a converts the data 130a from the EXTCOM protocol to the HL7 protocol. The first integration engine 160a then transmits the converted data 130b to the patient monitor 106 for display. To perform the conversion, the first integration engine 160a may include instructions that specify how certain EXTCOM labels are to be translated into HL7 labels. The instructions may also specify the order or placement of the fields within the HL7 message. The instructions may further specify additional information to be added to the HL7 message (if known) or default information that is to be provided to ensure the HL7 message is verified as being proper. In some instances, the instructions may also provide for unit conversion from a first unit type used for EXTCOM to a second unit type used for HL7. Moreover, the instructions at the integration engine 160a may also provide a translation of drug names (or abbreviations) used in the EXTCOM protocol to corresponding drug names (or abbreviations) used in the HL7 protocol.

Also in the illustrated example, the RFT machine 104 transmits renal failure therapy progress data 140a that is formatted in the EXTCOM protocol to the RFT gateway 114. The second integration engine 160b converts the data 140a from the EXTCOM protocol to the HL7 protocol. The second integration engine 160b then transmits the converted data 140b to the patient monitor 106 for display. The integration engine 160c receives the data 130b and 140b in the HL7 format and determines whether derivative data is to be determined. The integration engine 160c also causes the patient monitor to display the data 130b and 140b. In some instances, the integration engine 160c may be configured to convert the data 130b and 140b into another protocol that is compatible with the patient monitor 106 before the data can be displayed.

CONCLUSION

It will be appreciated that all of the disclosed methods and procedures described herein can be implemented using one or more computer programs or components. These components may be provided as a series of computer instructions on any conventional computer-readable medium, including RAM, ROM, flash memory, magnetic or optical disks, optical memory, or other storage media. The instructions may be configured to be executed by a processor, which when executing the series of computer instructions performs or facilitates the performance of all or part of the disclosed methods and procedures.

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims.

It should be appreciated that 35 U.S.C. 112(f) or pre-AIA 35 U.S.C 112, paragraph 6 is not intended to be invoked unless the terms "means" or "step" are explicitly recited in the claims. Accordingly, the claims are not meant to be limited to the corresponding structure, material, or actions described in the specification or equivalents thereof.

The invention is claimed as follows:

1. A medical data integration apparatus comprising:
    a screen configured to display a user interface;
    a gateway interface communicatively coupled to at least one medical gateway via a network; and
    a data processor communicatively coupled to the screen and the gateway interface, the data processor configured to
        receive a patient identifier related to a patient,
        transmit a request message with the patient identifier via the gateway interface to the at least one medical gateway,
        receive, from the at least one medical gateway, (i) infusion therapy progress data that is related to the patient identifier, the infusion therapy progress data generated by an infusion pump, (ii) renal failure therapy progress data that is related to the patient identifier, the renal failure therapy progress data generated by a renal failure therapy machine, and (iii) physiological data that is related to the patient identifier, the physiological data generated by at least one physiological sensor, determine fluid balance data based on a difference between (i) and (ii), display, via the user interface, the fluid balance data in conjunction with (i) and (ii), and display, via the user interface, hemodynamic information using (iii).

2. The apparatus of claim 1, wherein the data processor is configured to display at least some of the infusion therapy progress data within an infusion timeline of the user interface, and display at least some of the renal failure therapy progress data within a renal failure therapy timeline of the user interface that is aligned with the infusion timeline.

3. The apparatus of claim 1, wherein the data processor is configured to display the physiological data within at least one physiological timeline of the user interface.

4. The apparatus of claim 1, wherein the infusion therapy progress data includes at least one of an infusion rate, an infusion dosage, an infusion progress time, an operational status, or a volume of fluid remaining to be infused.

5. The apparatus of claim 1, wherein the renal failure therapy progress data includes at least one of a fill rate, a dwell time, a drain or fluid removal rate, a blood flow rate, an effluent dose, an ultrafiltration removal rate, a dialysate removal rate, a total dialysate infused, a dialysate flow rate, a replacement pre-dilution rate, a replacement post-dilution rate, a patient weight balance, a return pressure, an excess patient fluid sign, a filtration fraction, a time remaining, a dialysate concentration, or a dialysate name.

6. The apparatus of claim 1, wherein the physiological data includes at least one of heart rate data, temperature data, pulse oximetry data, weight data, glucose data, cardiac output data, respiratory rate data, or blood pressure data.

7. The apparatus of claim 1, wherein the data processor is further configured to:
receive at least one of urine data or fluid drain data related to the patient; and
add the at least one of urine data or fluid drain data to (ii) before determining a difference with (i).

8. The apparatus of claim 1, wherein the infusion therapy progress data includes infusion therapy progress data from two or more infusion pumps.

9. The apparatus of claim 1, wherein the infusion therapy progress data includes at least one of alarm information or event information, and
wherein the data processor is further configured to display the at least one of alarm information or event information within the user interface.

10. The apparatus of claim 1, wherein the patient identifier is received from a bar code scanner.

11. A medical data integration apparatus comprising:
a screen configured to display a user interface;
a gateway interface communicatively coupled to at least one medical gateway via a network; and
a data processor communicatively coupled to the screen and the gateway interface, the data processor configured to
receive a patient identifier related to a patient,
transmit a request message with the patient identifier via the gateway interface to the at least one medical gateway,
receive, from the at least one medical gateway, (i) an infusion rate and an infusion treatment time that is related to the patient identifier, the infusion rate and the infusion treatment time generated by an infusion pump, (ii) a fluid removal rate and a renal failure treatment time that is related to the patient identifier, the fluid removal rate and the renal failure treatment time generated by a renal failure therapy machine, and (iii) physiological data that is related to the patient identifier, the physiological data generated by at least one physiological sensor,
determine fluid balance data based on a difference between (i) and (ii),
display, via the user interface, the fluid balance data, and
display, via the user interface, hemodynamic information using (iii).

12. The apparatus of claim 11, wherein the data processor is further configured to:
multiple the infusion rate by the infusion treatment time to determine a total volume of fluids infused;
multiple the fluid removal rate by the renal failure treatment time to determine a total volume of fluids removed; and
determine the fluid balance data by calculating a difference between the total volume of fluids infused and the total volume of fluids removed.

13. The apparatus of claim 12, wherein the data processor is further configured to:
receive at least one of urine data or fluid drain data related to the patient; and
add the at least one of urine data or fluid drain data to the total volume of fluids removed.

14. The apparatus of claim 11, wherein the data processor is further configured to:
receive varying fluid removal rates over respective renal failure treatment times;
receive varying infusion rates over respective infusion treatment times;
determine a total volume of fluids removed using the varied fluid removal rates and the corresponding respective renal failure treatment times;
determine a total volume of fluids infused using the varied fluid infusion rates and the corresponding respective infusion treatment times; and
determine the fluid balance data by calculating a difference between the total volume of fluids infused and the total volume of fluids removed.

15. The apparatus of claim 11, wherein the data processor is configured to display the infusion rate within an infusion timeline of the user interface, and display the fluid removal rate within a renal failure therapy timeline of the user interface that is aligned with the infusion timeline.

16. The apparatus of claim 11, wherein the data processor is configured to display the physiological data within at least one physiological timeline of the user interface.

17. The apparatus of claim 11, wherein the physiological data includes at least one of heart rate data, temperature data, pulse oximetry data, weight data, glucose data, cardiac output data, respiratory rate data, or blood pressure data.

18. The apparatus of claim 11, wherein the infusion rate includes infusion rates from two or more infusion pumps.

19. The apparatus of claim 11, wherein the infusion rate is received in conjunction with at least one of alarm information or event information, and
   wherein the data processor is further configured to display the at least one of alarm information or event information within the user interface.

20. The apparatus of claim 11, wherein the renal failure therapy machine includes a hemodialysis machine, a hemofiltration machine, a hemodiafiltration machine, a continuous renal replacement therapy ("CRRT") machine, or a peritoneal dialysis ("PD") machine.

* * * * *